United States Patent [19]

Hood et al.

[11] Patent Number: 4,886,743

[45] Date of Patent: Dec. 12, 1989

[54] DIAGNOSTIC REAGENTS BASED ON UNIQUE SEQUENCES WITHIN THE VARIABLE REGION OF THE T CELL RECEPTOR AND USES THEREOF

[75] Inventors: Leroy E. Hood, Pasadena; Irving L. Weissman, Stanford; Michael S. McGrath, Menlo Park, all of Calif.

[73] Assignee: California Institute of Technology, Pasadena, Calif.

[21] Appl. No.: 726,502

[22] Filed: Apr. 24, 1985

[51] Int. Cl.[4] .................. C12Q 1/68; G01N 33/53; G01N 33/569; C07K 7/10

[52] U.S. Cl. .................................... 435/5; 435/6; 435/7; 435/29; 530/387; 530/326; 935/78; 935/104; 935/11; 935/12; 436/548; 436/813; 436/536; 436/52; 436/63; 436/506; 436/508; 436/509

[58] Field of Search .................................. 435/5-7, 435/29, 810; 436/501, 503, 504, 506, 508, 509, 518, 536, 548, 813, 820, 52, 63; 935/11, 12, 78, 25, 80, 81, 104; 530/326, 387, 388; 536/27

[56] References Cited

U.S. PATENT DOCUMENTS

| | | | |
|---|---|---|---|
| 4,364,937 | 12/1982 | Kung et al. | 935/104 X |
| 4,550,086 | 10/1985 | Reinherz et al. | 935/104 X |
| 4,582,788 | 4/1986 | Erlich | 436/504 X |
| 4,670,382 | 6/1987 | Buckley et al. | 935/104 X |
| 4,673,971 | 6/1987 | Fradet et al. | 935/104 X |
| 4,713,332 | 12/1987 | Mak | 935/12 X |

OTHER PUBLICATIONS

Yanagi, Y. et al., *Nature*, vol. 308, Mar. 1984, pp. 145-149.
Hedrick, S. M. et al., *Nature*, vol. 308, Mar. 1984, pp. 149-158.
Hood, L. et al., *Cell*, vol. 40, Feb. 1985, pp. 225-229.
Siu, G. et al., *Cell*, vol. 37, Jun. 1984, pp. 393-401.
Patten, P. et al., *Nature*, vol. 312, Nov. 1984, pp. 40-46.

*Primary Examiner*—Johnnie R. Brown
*Assistant Examiner*—Jeremy M. Jay
*Attorney, Agent, or Firm*—John P. White

[57] ABSTRACT

This invention provides a reagent capable of binding to T cells and having specificity for a unique sequence within the variable region of the $\beta$ chain of the T cell receptor, the presence of increased number of T cells carrying the unique sequence relative to the number of T cells carrying the sequence present in a normal subject being associated with a specific disease. Specific diseases such as human cancers, e.g. lymphomas; auto-immune diseases, e.g. rheumatoid arthritis; Alzheimer's disease; infectious diseases, e.g. those caused by bacteria, yeast or parasite; or allergies, may be diagnosed as follows. A suitable sample containing T cells is obtained from a subject. The sample is contacted under appropriate conditions with such a reagent. If the subject's T cells contain the unique sequence, a detectable complex is formed between the reagent and T cells which contain the sequence. By quantitatively determining the number of T cells containing the sequence present in the complex formed and comparing this number with the number of T cells carrying the sequence determined for a normal subject, the disease with which the unique sequence is associated may be diagnosed. Similar reagents and methods may also be used to detect organ transplant rejection.

57 Claims, 7 Drawing Sheets

```
        G G G A C A G G G G G C
3H.25   GLY
1.9.2       THR GLY
EI          THR GLY GLY
86TI    GLY GLN GLY
HDSII       GLN GLY
TB12            GLY
ARI       ASP
```

} 1
} 2
} 3

Dβ2.1

```
        G G G A C T G G G G G G C
C5      GLY THR GLY GLY
BW5147      THR
LB2         LEU
TB2         LEU GLY
TB12            GLY
TB21      ASP TRP GLY GLY
2B4             TRP
TB3             TRP
```

| | |
|---|---|
| GERMLINE | G G G A C A G G G G G C |
| 3H.25 | T T C ——— |
| 1.9.2 |       C A A ——————— G |
| E1 |       G C                C T |
| 86T1 | C A C ————————— T |
| HDS11 |           ————————— G C |
| TB12 |        G A T G T ——— |
| AR1 | G G T C ——————— A |

Dβ2.1

| | |
|---|---|
| GERMLINE | G G G A C T G G G G G G C |
| C5 | ————————— G C T G |
| BW5147 | C A G A T A —— A G T |
| LB2 |   A T A A ——————— C |
| TB2 |   G G T G A ————— C T T T |
| TB12 |      G A T G ————— C |
| TB21 |     G T C ——————— C G G |
| 2B4 |        A ——— A G |
| TB3 |    C A A G T ——— |

DIAGNOSTIC REAGENTS BASED ON UNIQUE SEQUENCES WITHIN THE VARIABLE REGION OF THE T CELL RECEPTOR AND USES THEREOF

BACKGROUND OF THE INVENTION

T cells are derived from the thymus and accordingly they are called T cells. They circulate freely through the blood and lymphatic vessels of the body, and so are able to detect and react against foreign invaders, i.e. viruses, allergens, tumors and autoantigens. Despite their uniform morphology under microscope, T cells consist of a heterogeneous population of cells with several distinct functional subsets called helpers, suppressors and killers [Kung, P. S. and Goldstein, G., Vox Sanquinis 39:121 (1980); Reinherz, E. L. and Schlossman, S. F., Cell 39:821 (1980).]

Through a recognition system called the T cell antigen receptor, T cells are able to detect the presence of invading pathogens and direct release of multiple, distinct T cell lymphokines called T cell factors, which instruct B lymphocytes to initiate or suppress antibody production, and regulate the white blood system in producing more phagocytes and other white cells to neutralize the pathogens, and destroy tumor cells and virally infected cells. Thus, the detection and binding of pathogens by T cells is linked to the triggering of T cell factor release and to the cascade of host defense actions initiated by these factors [Kung, P. S. and Goldstein, G., Vox Sanquinis 39:121 (1980); Reinherz, E. L. and Schlossman, S. F., Cell 19:821 (1980).]

T cell antigen receptors are different from other T cell surface markers in two major ways: (a) there are millions of distinct T cells in the body involved in disease fighting, and each T cell clone bears a unique T cell antigen receptor [Fathman, C. G. and Frelinger, J. G., Ann Rev. Immunol. 1:633 (1983),] and b) T cell antigen receptors have a known function in antigen binding. The functions of other T cell surface markers identifiable by commercially available OKT TM and Leu TM monoclonal antibodies remain largely unknown. These markers do not have the structural variabilities found in the T cell antigen receptor. Additionally, it appears that the receptor is the only molecule truly specific for T cells [Meuer, S. C., et al., Ann. Rev. Immunol. 2:23 (1984).]

Since T cells carry out a variety of regulatory and defense functions, they play a central role in immunologic responses. These responses include destroying self cells which have been virally or neoplastically transformed (T killer cells), helping B cells which make antibody molecules to differentiate and express their secreted gene products (T helper cells) and suppressing immune responses (T suppressor cells). Each of these categories of T cells is highly specific and the specificity is mediated through their T cell antigen receptor molecules. Therefore, an understanding of the T cell receptor molecules and their gene structure is essential to understanding the specificity and regulation of human immune responses.

The monoclonal antibody reagent market for T cell subset typing has grown to $20 million from a zero base in the four years since mid-1980. This growth reflects the demand for assays to monitor the status of T cell immunity which is directly involved in acute and chronic diseases [Kung, P. S., et al., International J. Dermatol. 22:67 (1983).] Prior to the advent of hybridoma technology a group of bioassays was developed in research laboratories intended to assess helper, suppressor and killer T cell activity. These bioassays are time consuming, tedious and labor intensive, usually taking more than a week to complete. As a result bioassays never generated a significant commercial volume.

A breakthrough occurred in the late 1970's when it was discovered that T cells bear several surface markers which are uniquely expressed, and monoclonal antibodies were generated against these markers. After extensive study in research laboratories, it was determined that monoclonal antibodies could be used to enumerate total T cells, helper cells and killer/suppressor T cells. These monoclonal antibody-based T cell typing tests when used with a flow cytometer have gained acceptance in laboratories around the world.

Monoclonal antibodies against these T cell surface markers are marketed by Johnson & Johnson (under the trademark Orthoclones OKT series), and by Becton Dickinson and Company (under the trademark Leu series). These antibodies are able to identify two major T cell functional subsets, called helpers or killer/suppressors, which account for 65% and 35% of total circulating T cells, respectively.

The first generation of OKT/Leu monoclonals has serious limitations. They cannot further distinguish killer T cells from suppressor T cells, Class I killers from Class II killers, or different helper, suppressor subtypes known to exist. Moreover, these monoclonals detect antigens which are not disease specific [Kung, P. S., et al., International J. Dermatol. 22:67 (1983).]

In about 1984 an important discovery was made by a team of scientists, headed by Dr. Tak Mak, at the Ontario Cancer Institute [Nature 308: 145 (1984)]. This team succeeded in isolating and sequencing the gene encoding the $\beta$ chain of the human T cell antigen receptor. The present invention has resulted from the unexpected discovery, made in the course of extending the work of Dr. Mak and others, that there exists a limited repertoire of $V_\beta$ gene segments and that the unique sequences contained within the gene and therefore within the amino acid sequence of the receptor which is encoded thereby may be used to diagnose human disease.

Thus, although others [e.g. Minden, M. D., et al., Proc. Nat'l. Acad. Sci. USA 81: 1224 (1984); Jones, N. et al., Science 227:311 (1985) and Acuto, O. et al., Proc. Nat'l. Acad. Sci. USA 81:3851 (1984)] have prepared monoclonal antibodies or nucleic acid probes specific for the variable region of the $\beta$ chain of the T cell antigen receptor, including amino acid sequences near the N-terminus of the variable region, such antibodies or probes have not been shown or suggested to be associated with specific disease states. Moreover, in the absence of an understanding of the limited number of such variable regions, one of ordinary skill in the art to which this invention pertains would not expect such to be the case. Thus, this invention is directed to the discovery that reagents specific for the variable region may be used to diagnose diseases or detect organ transplant rejection.

SUMMARY OF THE INVENTION

A specific disease of interest may be diagnosed in a subject as follows. A suitable sample containing T cells is obtained from a subject. The sample is contacted under suitable conditions with a reagent capable of binding to T cells and indicative of the presence of a unique amino acid sequence within the variable region of the β chain of the T cell receptor, the presence of an increased number of cells carrying the unique sequence relative to the number of cells carrying the sequence present in a normal subject being associated with the specific disease of interest. If the unique sequence is present, a detectable complex is formed between the reagent and T cells which contain the unique sequence and which are present in the sample. By quantitatively determining the amount of complex present and comparing the amount so determined with the amount determined for a normal subject using the same method, the disease of interest is diagnosed.

Numerous diseases may be so diagnosed. These include various forms of cancer, autoimmune diseases, infectious diseases and allergies. In addition, the method of this invention may be used to detect transplant rejection.

Finally, the invention provides reagents such as serum-derived or monoclonal antibodies and DNA or RNA probes which are useful in human disease diagnosis. Such reagents are characterized by having specificity for a unique sequence contained within the variable region of the β chain of the T cell receptor, the presence of increased copies of the unique sequence relative to the number of copies present in a normal subject being associated with a specific disease of interest.

BRIEF DESCRIPTION OF THE FIGURE

FIG. 1a. DNA sequence of eight $V_\beta$ genes. All cDNA libraries were constructed in the λgt10 cloning vector by a modification of the method of Huynh et al.[63]. Libraries were screen with a $^{32}$p-labeled $C_{62}$ cDNA probe, positive clones were isolated and cDNA inserts were subcloned into the M13mp8 or mp10 vectors. The $V_{62}$ genes of each subclone were sequenced on both strands by the dideoxynucleotide primers. The sequences are displayed with the $V_{62}$ and $J_{62}$ gene segments and D regions aligned separately. L refers to the nucleotides encoding the leader peptide. The TB23 subclones contained only a $V_{62}$ gene segment. The identity between the $V_{62}$ segments employed by 1.9.2 and BW5147 is indicated by dots. The cDNA obtained from AR1 contained only a portion of a $V_{62}$ gene segment beginning at position 161. For purposes of sequence alignment, the 5' portion of the homologous $V_\beta$ gene segment published previously[33] has been added.

FIG. 1b. The translated protein sequences of 15 $V_\beta$ gene segments. The DNA sequences of the eight $V_\beta$ gene segments shown in FIG. 1a, as well as seven $V_\beta$ gene segments published previously were translated and aligned to each other to maximize sequence homology. See Table 1 for the source of each sequence.

FIG. 2. The D region for 15 $V_\beta$ genes may arise from just two $D_\beta$ gene segments. The D regions shown in FIG. 1a and those published previously were aligned to either $D_{\beta1.1}$ or $D_{\beta2.1}$. The regions homologous to either $D_\beta$ gene segment are represented by a straight line. The additional nucleotides flanking the germline $D_\beta$ sequences are presumed to be added by N-region diversity. The D region employed by TB12 can be derived from either $D_{\beta1.1}$ or $D_{\beta2.1}$ and is so indicated.

FIG. 3. The $D_\beta$ gene segments may be joined to $V_\beta$ gene segments in all three translational reading frames. Numbers to left of brackets identify different reading frames.

FIG. 4. Variability plot of $V_\beta$ and $V_H$ segments. Variability at each amino acid position N is calculated as:

$$\text{Variability } N = \frac{\text{number of different amino acids that occur at } N}{\text{frequency of most commonly occurring amino acid at } N}$$

Figure 1:
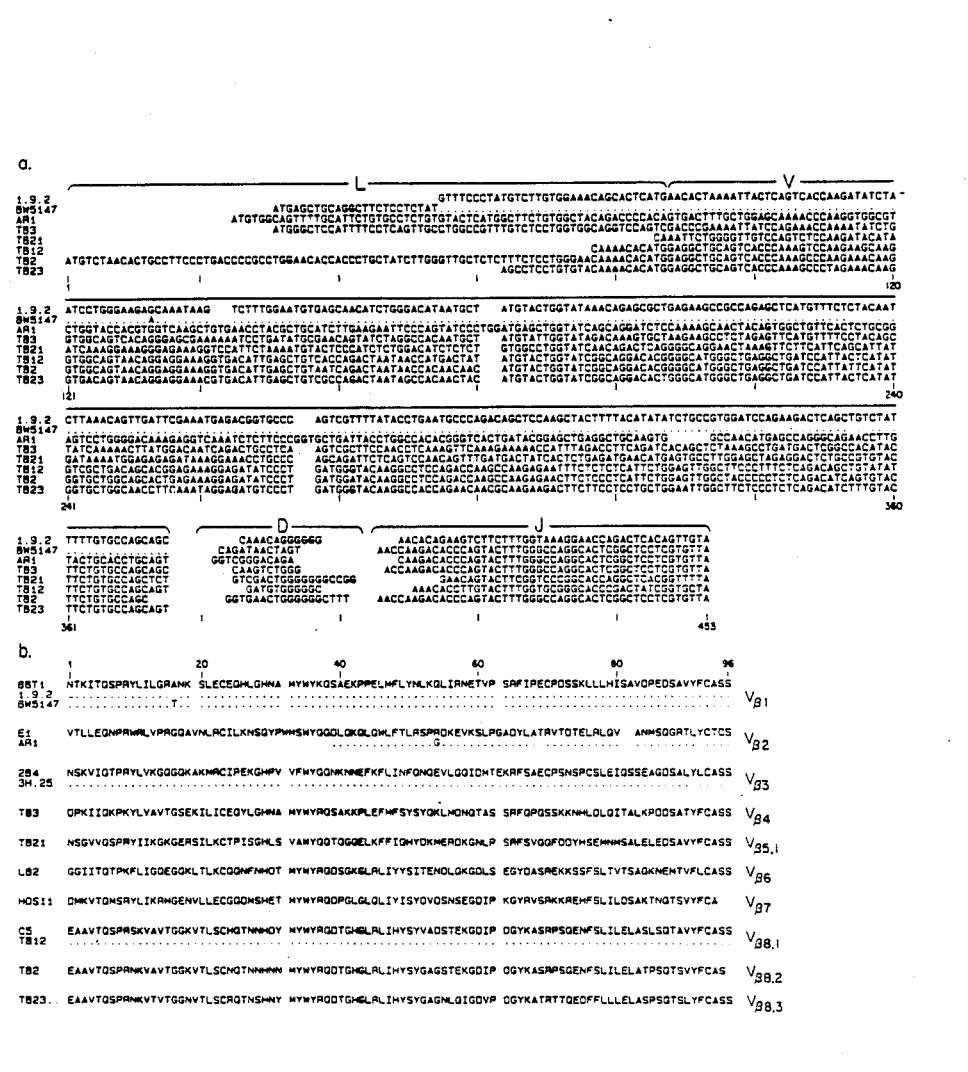

Hypervariable regions can be defined empirically as a set of residue positions whose average variability is greater than the mean variability of the entire sequence. The sequences used are all those available from the Protein Information Resource of the National Biomedical Resource Foundation and GenBank. (a) The translated sequence of the ten distinct $C_\beta$ gene segments shown in FIG. 1b. (b) Eighteen α amino blocked human $V_H$ sequences. (c) Thirty-one human $V_H$ sequences representing sequences blocked and unblocked at the α amino position.

Figure 5:
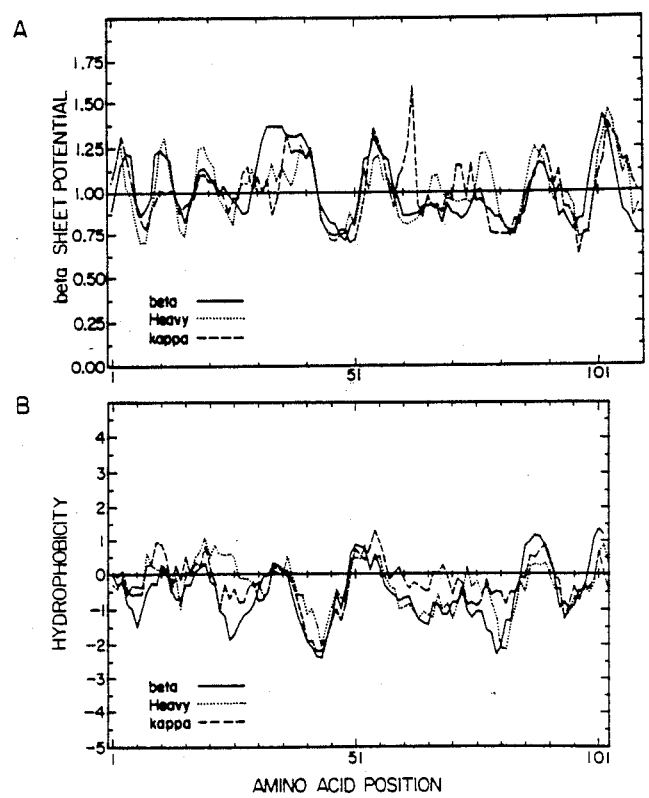

FIG. 5. Secondary structure analyses of $V_\beta$, $V_H$ and $V_K$ segments. (a) β-pleated sheet potential plots, using the method of Chou and Fassman.[58] (b) Hydrophobicity plots using the scale of Kyte and Doolittle.[59] Both analyses were based upon the average value at each position for 55 $V_H$ regions, 100 $V_K$ regions and 10 $V_\beta$ regions.

Figure 6:
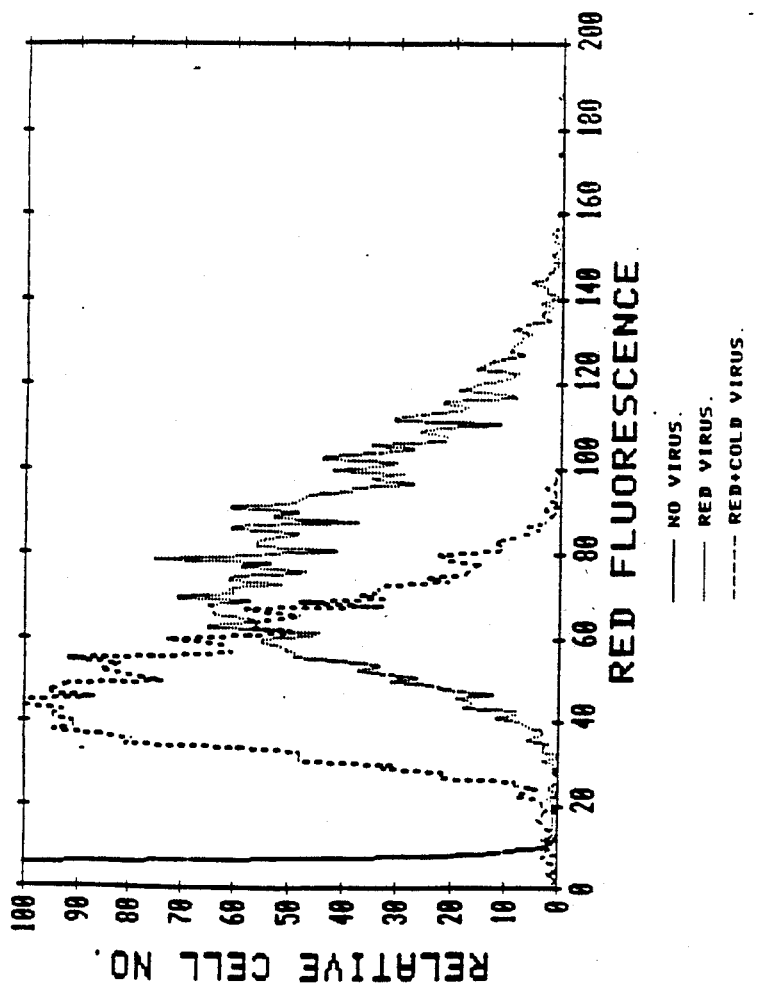

FIG. 6. HTLV-I Binding to the Jurkat T Lymphoma Cell Line. HTLV-I was obtained from MT-2 supernatants, and virus was concentrated and purified as previously described (3); HTLV-I was labeled with 10 micrograms/ml of rhodaminated octyl decanoic acid (reference 39) with virus at a concentration of 1 A260 unit/ml. Virus in PBS pH 7.4 was incubated with this rhodamine conjugated fatty acid for 1 hour at 37° C., and unbound fatty acid was removed by passing this virus preparation over a delipidated BSA affinity column. 0.1 A260 unit of this labeled virus was incubated with $5 \times 10^5$ Jurkat cells, for 1 hour at 4° C. prior to analysis on an Ortho cytofluorograph. The amount of rhodamine-labeled virus bound per cell was compared with unlabeled cells, and cells which had been exposed to an equivalent amount of unlabeled HTLV-I as a competitor.

Figure 7:
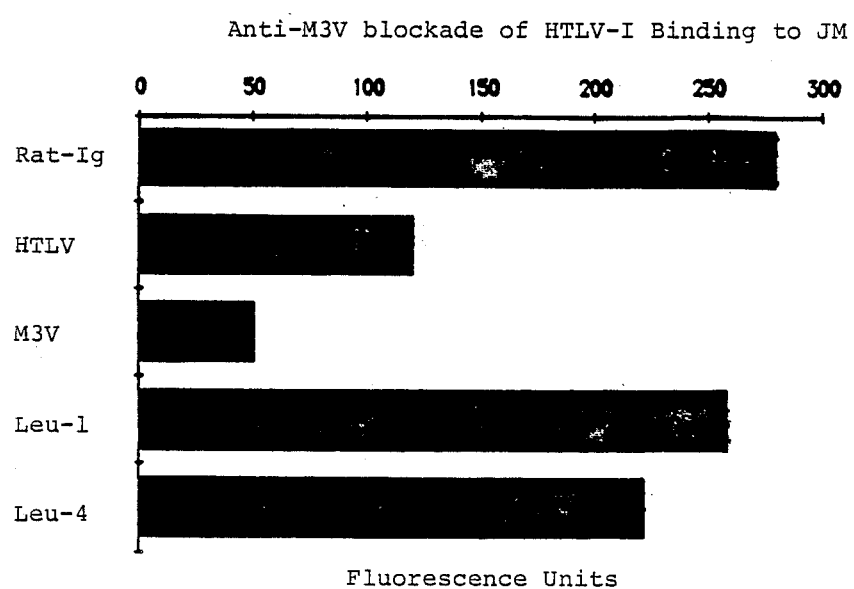

FIG. 7. Anti-M3V (Clone 43) Blockade of HTLV-I Binding to JM Cells. Cytofluorographic analysis of rhodamine-labeled HTLV-I binding and blockade of that binding with monoclonal antibodies was carried out as described in FIG. 1 to the JM cell line. $5 \times 10^5$ JM cells were preincubated with anti-Leu-1, anti-Leu-4, anti-M3V (clone 43) or negative control (gamma 2A) rat monoclonal antibodies (2 micrograms of each antibody in 50 microliters). This preincubation was at 37° C. in the absence of sodium azide, for 1 hour prior to the addition of 0.1 A260 unit of rhodamine-labeled HTLV-I, which was incubated with this group of cells at 4° C., also in the absence of azide. The median amount of fluorescence bound per cell which had also been exposed to an equal (0.1 A260 unit) of unlabeled HTLV-I.

DETAILED DESCRIPTION OF THE INVENTION

This invention provides a method of diagnosing a specific disease of interest in a subject. The method involves the following steps:

a. obtaining from the subject a suitable sample containing T cells;

b. contacting the sample under appropriate conditions with a reagent capable of binding to T cells and indicative of the presence of a unique amino acid sequence within the variable region of the chain of the T cell receptor, the presence of an increased number of cells carrying the unique sequence relative to the number of cells carrying the sequence present in a normal subject being associated with the specific disease of interest, so as to form a detectable complex between the reagent and T cells which contain the unique sequence and which are present in the sample; and c. quantitatively determining the number of T cells carrying the sequence present in the complex, comparing the number so determined with the number of T cells carrying the sequence determined for a normal subject using the same procedure and thereby diagnosing the disease of interest.

Examples of specific diseases of interest which may be diagnosed using the method of this invention include various forms of human cancer, e.g. breast cancers, colon cancers, lung cancers, lymphomas, hepatomas and leukemias; various autoimmune diseases, e.g. rheumatoid arthritis, type 1 diabetes, multiple sclerosis, systemic lupus erythematosis, aplastic anemia, autoimmune hemolytic anemia, immune thrombocytopenic purpara, graft vs host disease or other T cell mediated autoimmune diseases and myasthenia gravis or Graves disease; nephritis, vasculitis; myocarditis; myositis; colitis; psoriasis; Alzheimer's disease and other degenerative diseases of the nervous system; Kaposi's sarcoma; Hodgkin's disease; Ataxia telangectasia: Wiskott Aldrich syndrome; AILD (augio Immunoblastic lymphadenopathy with Dysproteinemia); various infectious diseases such as those caused by viruses, e.g. HTLV-I, HTLV-III (LAV or ARV), hepatitis A, hepatitis B and cytomegalovirus, by a yeast, e.g. one of the genus Candida, by a parasite, e.g. schistosome, filaria (Brugia malagi) or a mycobacterium, trichinosis, protozoans (trypanosomes) which cause sleeping sickness and by a bacterium, e.g. one which produces tetanus toxoid; and allergies, e.g. delayed type hypersensitivity or contact hypersensitivity involving T cells.

Although it is contemplated that the subject invention will have applicability for subjects in addition to human beings, such as domesticated animals, e.g. dogs, cats, cows and pigs, the invention is likely to be of greatest value, particularly in the near future, in the diagnosis of human disease. Similarly, although it is contemplated that suitable samples from the subject may take many forms, it is likely that whole blood and tissue, e.g. tissue section, samples will be used most frequently given the present state of the art. However, it is contemplated that additional types of samples, such as urine, colostrum, bone marrow, cerebral spinal fluid or joint fluid, may be used.

This invention utilizes the presence of unique amino acid sequences (or the unique nucleic acid sequences which encode them) within the T cell receptor and more particularly within the variable region of the β chain of the T cell receptor as markers for disease diagnosis. Specifically, the amino acid sequences so utilized are ones, the presence of which an increased number of T cells relative to the number of T cells carrying the sequence which are present in a normal subject, are associated with specific diseases. A suitable sample containing T cells is contacted under appropriate conditions with a reagent capable of binding to T cells and indicative of the presence of the unique amino acid sequence, either directly, or indirectly through the presence of a nucleic acid sequence encoding the amino acid sequence. Formation of a detectable complex between the reagent and T cells present in the sample indicates the presence of the unique sequence. By quantitatively determining the number of T cells present in complexes so formed and comparing the number with the number of T cells carrying the sequence determined for a normal subject, one may diagnose the disease of interest.

Although it is contemplated that any unique amino acid sequence present in the T cell receptor in increased copies in a disease state may be used in the practice of the subject invention, the presently preferred sequences are those present within the variable region of the β chain of the T cell receptor, including both those which have already been identified and those which will be identified in the future. Presently the preferred amino acid sequences are those present within about the first 30 amino acids located at the N-terminus of the variable region of the β chain of the T cell receptor. However, the precise location is not crucial; rather the ability of the sequence to serve as a unique marker is the critical factor. In general to be useful as a marker, the amino acid sequence will be at least 10 amino acids in length, i.e. sufficiently long to include an epitope to which an antibody may be raised or to be encoded by a nucleic acid sequence i.e. at least about 30 base pairs) with which a DNA or RNA hybridization probe may hybridize.

Merely by way of example, one such unique amino acid sequence is the following:

Gly-Val-Ile-Gln-Ser-Pro-Arg-His-Glu-Val-Thr-Glu-Met-Gly-Gln-Glu-Val-Thr-Leu-Arg-Cys.

This sequence is present at the N-terminus of the variable region of the β chain of the T cell receptor which is present in the surface of T cells and which is associated with both leukemia and lymphoma. Thus, its presence in a subject on increased numbers of T cells relative to a normal subject indicates a disease state in the subject.

Such unique sequences may be used to raise antibodies, either serum or monoclonal, using methods well known to those of ordinary skill in the art and the resulting antibodies used as reagents to detect T cells having such sequences present on their surface by contacting the cells with the antibodies under appropriate conditions, such conditions also being well known in the art.

Alternatively, DNA or RNA hybridization probes which are complementary to the DNA or RNA sequence which encodes all or a portion of the unique amino acid sequence may be prepared, again using well known methods such as chemical or enzymatic synthesis. The DNA or RNA hybridization probes are used as reagents to detect T cells which have such DNA sequences within them by contacting the , cells under appropriate conditions which also are known to those of ordinary skill in the art.

In order to practice the invention it is necessary that the complexes which result from contacting T cells with the reagents of this invention be detectable. One well known method for accomplishing this is to employ a detectable moiety as a marker. Thus, for serum or monoclonal antibodies the detectable moiety may be a flourescent dye, radioactive isotope, an enzyme which catalyzes a reaction producing a detectable product, biotin or a metal ion detectable by nuclear magnetic resonance. Similar detectable moieties may be used with DNA or RNA hybridization probes.

The quantitative determination of the amount of complex formed both in a sample from a subject under examination and in a sample from a normal subject may be accomplished using methods which depend upon the identity of the detectable moiety but which are nevertheless well known. Thus, if the detectable moiety is radioactive, a liquid scintillation counter may be employed. If the moiety is an enzyme such as horseradish peroxidase in a standard assay, a spectrophotomer may be employed. If the moiety is flourescent, a flourometer may be used. One particularly useful approach involves flourescence activated cell sorting by means of which the method may be conveniently, rapidly and accurately carried out.

This invention also provides a method for detecting organ transplant rejection in a subject into whom an organ from a different subject is transplanted. The method involves the following:

a. obtaining from the subject a suitable sample containing T cells;

b. contacting the sample under appropriate conditions with a reagent capable of binding to T cells and indicative of the presence of a unique amino acid sequence within the variable region of the β chain of the T cell receptor, the presence of an increased number of T cells carrying the unique sequence relative to the number of T cells carrying the sequence present in a normal subject being associated with organ transplant rejection, so as to form a detectable complex between the reagent and T cells which contain the unique sequence and which are present in the sample; and c. quantitatively determining the amount of the complex present, comparing the amount so determined with the amount determined for a normal subject using the same procedure and thereby detecting organ transplant rejection.

By way of example, the method of this invention may be used to detect rejection of heart, kidney or spleen transplants as well as bone marrow transplants or skin grafts all of which, for the purposes of this specification, are referred to as organ transplants.

In all other respects the method for detecting organ transplant rejection is identical to that for diagnosing specific diseases. Accordingly, the preceding discussion concerning sample form, detection methods and the like is applicable also to the detection of organ transplant rejection.

This invention also provides novel reagents useful in the methods which have been described herein above. Thus, the invention provides reagents capable of binding to T cells and having specificity for a unique amino acid sequence contained within the variable region of the βchain of the T cell receptor, the presence of increased numbers of T cells carrying the sequence in a subject relative to the number of T cells carrying the sequence present in a normal subject being associated with a specific disease of interest or being associated with rejection of a transplanted organ.

This invention further provides a novel polypeptide having the sequence:

Gly-Val-Ile-Gln-Ser-Pro-Arg-His-Glu-Val-Thr-
Glu-Met-Gly-Glu-Gln-Val-Thr-Leu-Arg-Cys.

This polypeptide may be chemically or enzymatically synthesized and antibodies to it prepared. Such antibodies detect lymphomas and leukemias. Additionally, a polydeoxyribonucleotide or polyribonucleotide complementary to the DNA sequence which encodes this polypeptide may be chemically or enzymatically prepared and used as a hybridization probe to detect these diseases. The preceding reagents, i.e. antibodies or nucleic acid hybridization probes, may be employed to screen lymphocytes derived from patients with a variety of diseases, including cancers, autoimmune diseases, allergies, infections and potential candidates for transplantation of organs. Using correlations found between one or more of these diseases and particular T cell $V_\beta$ gene segments, these reagents may be used to screen normal populations as potential candidates for these diseases, to monitor patients during the course of the disease or even to employ them as therapeutic carriers to deliver appropriate therapeutic agents.

THE ESSENTIAL OBSERVATIONS

Several key observations have been made. First, DNA sequences of eight $V_\beta$ gene segments randomly chosen from mouse T cells (primarily cDNA clones) have been determined. These T cells include functional helper and killer cells, T-cell tumors and thymocytes. These data taken together with seven sequences from the literature have allowed the determination that these 15 sequences are represented by eight different $V_\beta$ nucleotide sequences. One of these sequences is repeated three times, three sequences are repeated two times and six sequences are repeated a single time. These data permit one to ask a statistical question. Given a pool of different $V_\beta$ sequences exist such represented, how many different $V_\beta$ sequences exist such that the probability of drawing out the sets of identical sequences enumerated above is 95%. The answer to this simple question is that there are 21 $V_\beta$ genes in the mouse at 95% probability.

Second, seven of the eight distinct $V_\beta$ gene segment sequences have been cloned and used as probes to analyze the number of homologous $V_\beta$ gene segments in mouse liver DNA. These data taken together with other data from the literature permit one to say that seven of the eight V sequences are represented by just a single copy in the mouse genome and the remaining family is represented by three members. This very small family size is important, because it means that distinct $V_\beta$ gene segments differ markedly from one another and correspondingly, when they are translated into protein sequences, they will be quite different from one another. This also means that when peptide fragments are made from these distinct protein sequences, quite distinct and noncross-reactive sets of antibodies will be generated.

Third, there is very little polymorphism of the $V_\beta$ gene segments in different inbred strains of mice. This indicates that every mouse has essentially the same $V_\beta$ gene segments, and correspondingly DNA or antibody probes that are made against them will react with all different types of mice. It is contemplated that the same will be true of humans.

Fourth, somatic mutation in mouse $V_\beta$ genes is restricted entirely to the J and D gene segments. Indeed, the mouse $V_\beta$ gene segments employ an entirely new mechanism of somatic mutation that is not seen in any of the antibody gene families. This means that the subtle diversity that must be created in mouse T cell receptors to generate specificity differences in the β gene family resides in the J and D gene segments. This is exciting because it means that the DNA or antibody probes generated against the D and J regions will permit one to discriminate the finer subspecificities of the T cell receptors. Thus, for example, probes may be generated that are specific for various autoimmune diseases.

Fifth, the immunoglobulin genes employ a mechanism of somatic hypermutation to diversify their V genes throughout the entire length of the V gene. The $V_\beta$ genes do not employ this mechanism, and accordingly once the $V_\beta$ gene has been isolated and sequenced, antibodies and DNA probes may be made which will be directed against an invariant portion of the T-cell receptor. Thus, one will not have to worry that somatic mutation will render the DNA antibody reagents of this invention ineffective.

Experiments in the human T cell receptor system confirm the important generalizations drawn from the mouse system. First, in generating cDNAs from the series of randomly chosen tumors, the same $V_\beta$ gene segment has been repeatedly obtained. This indicates that there will be a relatively small number of $V_\beta$ gene segments in man. Second, the size of the only human $V_\beta$ gene family investigated is four, which is the size of the smallest $V_H$ gene family seen in immunoglobulin heavy chain genes. Once again this observation indicates that the size of the $V_\beta$ gene families in the human will be small. Third, the same $V_\beta$ has been isolated from two humans who are not related at all to one another, and it has been found that this $V_\beta$ gene is identical nucleotide for nucleotide in both of these unrelated people. This indicates that the range and extent of polymorphism in human T cell receptors is also very limited. Fourth, the fact that several different human $V_\beta$ gene segments from random tumors all have identical sequences once again indicates that there is not a somatic hypermutation mechanism in human $V_\beta$ genes. Finally, an N-terminal peptide to the human $\beta$ segment has been generated. After coupling to an appropriate carrier it has been used to raise monoclonal and polyclonal antibodies. These antibodies recognize specifically the $\beta$-polypeptide chain on the surface of intact T lymphoma cells. This critical observation demonstrates that antibodies against N-terminal peptides can be generated and used to identify the T-cell receptors that contain the particular $V_\beta$ segment.

The observations in mouse and humans taken together indicate that the $V_\beta$ gene segment repertoire in both animals is extremely limited, that the family size of $V_\beta$ is generally small and that there is no hypermutation to diversify the $V_\beta$ segments.

There are five features about the mouse and human T cell receptor systems that stand in striking contrast to features that would be expected from a study of immunoglobulin genes. First, there are a very small number of $V_\beta$ gene segments in the T cell receptor family, perhaps 29 or fewer at the 95% confidence level. In the immunoglobulin kappa and heavy chain gene families 200–300 V gene segments are estimated. Second, the sizes of the cross-hybridization families of $V_\beta$ gene segments are very small. Of the eight families identified, seven are single gene families and the remaining one is three gene families for the $\beta$ gene system. In contrast, the immunoglobulin heavy chain gene family has at least seven $V_H$ gene families which range from 4–50 or more, and the $V_\kappa$ family has at least ten $V_\kappa$ gene families which range in size from 5–25 with the exception of a single $V_\kappa$ gene family which has one member. Third, the V gene segments of the $\beta$ gene family of T-cell receptors show very little polymorphism. Their counterparts in the $V_\kappa$ and $V_H$ gene family show striking polymorphism. Fourth, there is a new somatic mutational mechanism that leads to increased diversity in the J and V gene segments. Indeed, T-cell receptor generation also employs two new combinatorial diversification mechanisms that are not seen in the immunoglobulin gene families. Accordingly, T-cells have enormous capacity for varying their D and J gene segments. Finally, there is a lack of somatic hypermutation in the $V_\beta$ genes that have been studied to date. In contrast, there are examples of enofmous hypermutation in all of the immunoglobulin gene families.

The existence of a small repertoire of $V_\beta$ gene segments in one of the two chains of the T cell receptor means that general diagnostic reagents may be constructed which will enable one to see all T cell receptors. Two approaches can be employed. First, one may translate the 5' $V_\beta$ gene segment sequence into protein sequence and synthesize the corresponding polypeptide fragment. This fragment can be coupled to an appropriate carrier protein and used to immunize mice or rabbits to generate monoclonal and polyclonal antibodies. It has already been demonstrated in one human case that such an N-terminal antibody can readily react with the T-cell receptor on the cell surface. Thus, these diagnostic antibodies can be used to quantitate the ratios in populations of T cells that have each of the various V gene segments. The ratios of these $V_\beta$ genes segments can then be correlated with different disease states. Second, the $V_\beta$ gene segments may be used to synthesize DNA probes which will uniquely characterize each of the distinct $V_\beta$ gene segments. Then DNA could be isolated from peripheral blood lymphocytes and the RNA derived from these populations of peripheral blood lymphocytes could be examined to determine what fraction contains or expresses particular $V_\beta$ segments.

These antibody or DNA reagents may then be used to screen normal individuals and patients with cancers, autoimmune diseases, allergies, infections and candidates for organ transplantation. The associations of particular $V_\beta$ gene segments with any of disease states will be noted. Then, apparent normal patients may be screened with the same reagents to predict the eventual acquisition of particular diseases. For particular disease states that are correlated with particular $V_\beta$ segments, the response of this disease state treatment would be monitored with such reagents. Eventually, these reagents may be used as molecular delivery systems to provide therapeutic agents specific for T cells associated with particular disease states. Thus, these reagents may be used as diagnostics for the screening of normal populations and the monitoring of pathologic states and as well.for therapeutic applications.

In principle, the limited number of different reagents could divide the entire population of T cell receptor genes into distinct classes. Since much of the diversity in the $V_\beta$ genes occurs in the D and J gene segments, one may synthesize peptides or DNA probes that correspond to certain D-J gene segments in an exacting way with precise types of diseases. Thus, one could have crude screening reagents that divide all subjects into a series of very general categories using the N-terminal based diagnostics, and then fine-tune the diagnostic or therapeutic procedure by making similar reagents against the D-J region which, it is contemplated, are correlated in a very precise way with the type of specificity that the T cell receptor sees.

EXPERIMENTAL DETAILS
FIRST SERIES OF EXPERIMENTS

Abstract

The sequences of eight cDNA clones containing $V_\beta$ genes of the mouse T-cell receptor have been determined and compared with seven $V_\beta$ genes reported in the literature. Among the 15 $V_\beta$ gene segments, one $V_\beta$ gene segment occurs three times, three are repeated twice and six are found just once. A statistical analysis of the frequency of finding identical $V_\beta$ gene segments with the sample analyzed to date implies that the total number of expressed $V_\beta$ gene segments is 21 or less. This estimate is much less than the number of germline $V_H$ and $V_\beta$ gene segments. DNA blotting studies also suggest that the $V_\beta$ gene segment repertoire is small. This result, in conjunction with the apparently low frequency of somatic hypermutation, suggests that $\beta$ chain somatic diversification is concentrated at the $V_\beta$-$D_\beta$-$J_\beta$ junctions. The $V_\beta$ and immunoglobulin V genes have very similar structural features and share many but not all mechanisms for diversification.

Introduction

The T cell receptor genes code for cell-surface glycoproteins that exhibit a striking structural and functional heterogeneity[1-3]. This genetic diversity is responsible for the ability of T cells to respond to a seemingly infinite number of antigens. T cell receptor molecules are integral membrane proteins, composed of $\alpha$ and $\beta$ chains, each in turn divided into variable and constant regions[1-3]. The variable region of each gene is presumed to form the antigen binding domain of the T cell receptor. The $\beta$ genes, located on chromosome 6 of the mouse[4,5], are the most thoroughly studied T-cell receptor genes. They are divided into distinct variable ($V_\beta$), diversity ($D_\beta$) and joining ($J_\beta$) gene segments that rearrange during T-cell development to form a $V_\beta$ gene that is associated with either of two constant ($C_{\beta 1}$ and $C_{\beta 2}$) genes.[6-12]

The $V_\beta$, $D_\beta$, and $J_\beta$ gene segments encode 93-95, 1-4 and 15-17 amino acids, respectively, and when assembled into a complete $V_\beta$ gene, encode the entire $\beta$ chain variable region[6-12]. There are six functional J gene segments clustered just 5' to each $C_\beta$ gene[6,8,9]. Two $D_\beta$ gene segments have been identified [10-11]. The $D_{\beta 1.1}$ gene segment is located upstream to the $J_{\beta 1}$ cluster and the $D_{\beta 2.1}$ gene segment lies upstream to the $J_{\beta 2}$ cluster[10,11]. The entire $D_{62\,1}$-$J_{\beta 1}$-$C_{\beta 1}$ gene cluster is located immediately 5' to the $D_{\beta 2}$-$J_{\beta 2}$-$C_{\beta 2}$ gene cluster[8]. An unknown number of $V_\beta$ gene segments reside upstream to the $D_{\beta 1}$-$J_{\beta 1}$-$C_{\beta 1}$ gene cluster. The general organization of the genes is similar to that of the immunoglobulin genes. Immunoglobulins, produced by cells of the B-lymphocyte lineage, are composed of heavy (H) and light (L) chains which fold into variable and constant domains. The $V_L$ genes are formed from $V_L$ and $J_L$ gene segments[13-15] and the $V_H$ genes are formed from $V_H$, $D_H$ and $J_H$ gene segments[16,17]. Like the T-cell receptor, immunoglobulins are capable of recognizing an immense number of different antigens. Consequently, both molecules may share similar strategies for diversification. Antibody diversity arises by a number of distinct mechanisms: (1) a multiplicity of germline gene segments; (2) combinatorial joining of different V, D and J gene segments[18,19]; (3) junctional flexibility at the sites of gene segment joining[19-21]; (4) N-region diversity which adds random nucleotides to either side of the D gene segment in the process of joining[22]; and (5) somatic hypermutation which can generate single nucleotide substitutions throughout the entire V gene[23,24].

T cell antigen recognition differs from that mediated by immunoglobulins in that T cells must recognize antigen in the context of a cell-surface molecule encoded by the major histocompatibility complex (MHC) a phenomenon termed MHC restriction.[25,26] T-cytotoxic ($T_C$) cells which are capable of killing virus infected and tumor cells, are mainly restricted by class I gene products of the MHC.[27] T-helper ($T_H$) cells are capable of enhancing B- or T-cell responses, are mainly restricted by class II MHC gene products.[28] It is unclear if T suppressor ($T_S$) cells which inhibit B- or T-cell responses, are restricted by MHC elements.[29] MHC molecules are extremely polymorphic in mice. The MHC restricting elements recognized by T cells are the allele-specific polymorphic determinants on each MHC molecule[30]. Therefore, T-cell receptor diversification must accommodate both antigen and MHC recognition.

In an effort to determine the extent of T-cell receptor diversity and its relationship to antigen/MHC recognition, eight $V_\beta$ genes from cDNA libraries of functional T cells and thymocytes have been analyzed. These $V_\beta$ gene sequences have been compared with seven from the literature. It has been found that: (1) the expressed $V_\beta$ gene repertoire is small, perhaps less than 21 members, (2) $V_\beta$ protein segments are structurally similar to immunoglobulin V segments, (3) each of the first four mechanisms for generating antibody diversity described above are employed by the $\beta$ genes of the T-cell receptor, and (4) T cells may join D gene segments in all three reading frames leading to additional somatic diversification of the 3' ends of the V genes and (5) there is no simple correlation between antigen and MHC specificity and the use of particular $\beta$ chain gene segments.

The $V_\beta$ gene family appears to employ a limited repertoire of expressed $V_\beta$ gene segments.

The nucleotide sequence of eight $C_\beta$ genes obtained from cDNA libraries of thymus cells, the pigeon cytochrome c reactive $T_H$ hybridoma 1.9.2 and a functional $T_C$ cell line specific for MHC alloantigens have been determined. The sequences of these $V_\beta$ genes were compared with each other and to seven additional $V_{62}$ genes taken from the literature (FIG. 1a, Table 1).[6,31-34] Of the 15 $V_\beta$ genes analyzed, six are from $T_H$ cells, two from $T_C$ cells, six from thymocytes and one is from a T-cell tumor (Table 1). The antigen/MHC specificities of the functional cells are listed in Table 1. The specific functions and thymocyte-derived $V_\beta$ genes are unknown. Since 99% of thymocytes do not migrate out of the thymus[35], some of thymocyte-derived $v_\beta$ genes may come from nonfunctional T cells. The $V_\beta$ gene segments of each of the 15 $V_\beta$ genes were translated into protein sequences and are shown in FIG. 1b. There are 10 distinct $V_\beta$ gene segment sequences found in the 15 $V_\beta$ genes analyzed. For reasons discussed below, the first seven of the $V_\beta$ gene segments listed in FIG. 1b are designated $V_{\beta 1-7}$ and the last three are designated $V_{\beta 8.1}$, $V_{\beta 8.2}$ and $V_{\beta 8.3}$. One $V_\beta$ gene segment is used three times ($V_{\beta 1}$) three are used two times ($V_{\beta 2}$, $V_{\beta 3}$, and $V_{\beta 8.1}$), and six are used once ($V_{\beta 4}$, $V_{\beta 5.1}$, $V_{\beta 6}$, $V_{\beta 7}$, $V_{\beta 8.2}$ and $V_{\beta 8.3}$). Moreover, when the sequences of seven additional $V_\beta$ genes isolated from six $T_H$ cells by our laboratory and others are included, 11 different $V_\beta$ gene segments are found to be employed in 22 rearranged genes.

gene segment family is 21 or less. This estimate of the mouse $V_\beta$ gene segment repertoire is much smaller than

TABLE 1

THE CHARACTERISTICS AND ORIGINS OR THE SEQUENCED $V_\beta$ GENES

| $V_\beta$ Gene | Class | Strain | Specificity Antigen/MHC | $V_\beta$ | $D_\beta$ | $J_\beta$ | Reference |
|---|---|---|---|---|---|---|---|
| 2B4 | $T_H$ | B10.A | Cytochrome C/I-$E_\alpha^\kappa E_\beta^\kappa$ | 3 | 2.1 | 2.5 | 6 |
| 1.9.2 | $T_H$ | B10.A[5R] | Cytochrome C/I-$E_\alpha^\kappa$,I-$E_\beta^b$ | 1 | 1.1 | 1.1 | * |
| 3H.25 | $T_H$ | C57BL/6 | Hen egg lysozyme/I-$A^b$ | 3 | 1.1 | 1.2 | 34 |
| C5 | $T_H$ | C57BL/6 | DNP-ovalbumin/I-$A^b$ | 8.1+ | 2.1 | 2.5 | 33 |
| E1 | $T_H$ | BALB/c | TNP**/I-$A^d$ | 2 | 1.1 | 2.2 | 33 |
| LB2 | $T_H$ | C57BL/6 | Chicken RBC***/I-$A^b$ | 6 | 2.1 | 2.3 | 33 |
| HDS11 | $T_C$ | BALB.B | H-$2^d$ | 7 | 1.1 | 2.6 | 32 |
| AR1 | $T_C$ | C57L | H-$2^d$ | 2 | 1.1 | 2.5 | * |
| 86T1 | Thymocyte | BALB/c | — | 1 | 1.1 | 1.3 | 31 |
| TB2 | Thymocyte | C57BL/ka | — | 8.2+ | 2.1 | 2.5 | * |
| TB3 | Thymocyte | C57BL/ka | — | 4 | 2.1 | 2.5 | * |
| TB12 | Thymocyte | C57BL/ka | — | 8.1 | 1.1 or 2.1++ | 2.4 | * |
| TB21 | Thymocyte | BALB/c | — | 5.1 | 2.1 | 2.6 | * |
| TB23 | Thymocyte | BALB/c | — | 8.3+ | ND | ND | * |
| BW5147 | Tumor | AKR | — | 1 | 2.1 | 2.5 | * |

+The three members of the $V_{\beta 8}$ subfamily are denoted $V_{\beta 8.1}$, $V_{\beta 8.2}$ and $V_{\beta 8.3}$
++So little of the $D_\beta$ gene segment remains in the rearranged $V_\beta$ gene that it is impossible to know which $D_\beta$ gene segment contributed the sequence.
*This paper.
**Trinitrophenol
***Red Blood Cell
ND Not Determined Six of the 11 different $V_\beta$ gene segments were employed more than once. Common $V_\beta$ gene segments occur in functional T cells, thymocytes and the T-cell tumor BW5147. The repeated use of $V_\beta$ gene segments in a sample of this size suggests that the repertoire of expressed $V_\beta$ gene segments is small. This hypothesis requires that all the $V_\beta$ gene segments are expressed randomly. By making this assumption, the question of the size of the $V_\beta$ gene segment repertoire can be addressed statistically.

If there are L species of $V_\beta$ gene segments and they are expressed with equal probability and are randomly selected from the pool, then the probability (p) of obtaining an observed result is $$p(m_1 m_2 \ldots, m_N) = \frac{1}{L^N} \cdot \frac{L!}{(L-M)!M!} \cdot \frac{N!}{(1!)_1^m \cdot (2!)_2^m \ldots (N!)_N^m} \cdot \frac{M!}{m_1! m_2! \ldots m_N!}$$

where
$m_1$=the number of different species found once;
$m_2$=the number of different species found twice;
$m_N$=the number of different species found N times;

$$N = \sum_{i=1}^{N} i \cdot m = \text{the total number of samples analyzed; and}$$

$$M = \sum_{i=1}^{N} m_i = \text{the number of different species found in the sampling.}$$

Conversely, given the observed result, the relative likelihood of the hypothesis that there are exactly L species in the pool is $$p(L) = \frac{1}{\sum_{L'=M}^{\infty} \frac{L'!}{L'^N(L'-M)!}} \cdot \frac{L!}{L^N(L-M)!}$$

For the data discussed above, N=22 and M=11. By choosing a range of values for L and testing each for the probability of arriving at the value M-11 for N=22, one finds that at the 95% confidence level, the size of the $V_\beta$ gene segment family is 21 or less. This estimate of the mouse $V_\beta$ gene segment repertoire is much smaller than the mouse immunoglobulin $V_H$ ($\simeq$100–300) or $V_\kappa$($\simeq$100–300) gene segment families [36,37], but larger than the mouse $V_{80}$ (2) repertoire[13]. However, mouse $\lambda$chains are expressed in only a few percentage of mature B cells, whereas $\beta$ chains are expressed in all $T_H$ and $T_C$ cells that have been analyzed[38,39].

We do not know if each $V_\beta$ gene segment is expressed with equal probability in the T-cell population or if the sampling of $V_\beta$ genes is entirely random. In fact, the relative occurrence of $V_\beta$ gene segments we observe can also be explained by the frequent use of a small subset of $V_\beta$ gene segments. However, the fact that we find identical $V_\beta$ gene segments employed by T cells that differ in their antigen recognition and MHC restriction as well as between functional T cells and unselected thymus cells (Table 1), indicates that the effective repertoire of expressed $V_\beta$ gene segments is probably very small. Accordingly, a large multiplicity of germline $V_\beta$ gene segments does not appear to be a major contributing factor in the generation of T-cell receptor diversity.

Most mouse $V_\beta$ gene segments exist as single gene subfamilies

Another method of estimating the size of the $V_\beta$ gene segment repertoire is to determine the number of cross-hybridizing $V_\beta$ gene segments in the mouse genome by using the isolated $V_\beta$ gene segments as specific hybridization probes. Although this approach is restricted to identifying $V_\beta$ gene segments that share extensive homology to the $V_\beta$ gene segments is obtained that can be compared to the number predicted statistically. When this type of analysis was carried out with mouse $V_H$ and $V_\kappa$ gene segment probes, all of the V gene segments were found to fall into one of several distinct multigene subfamilies[36,37]. In mice there appear to be at least seven $V_H$ subfamilies ranging in size from two to more than 40 members and at least five $V_\kappa$ subfamilies ranging in size from two to more than 20 members[36,37]. V gene segments with 75% or greater similarity have been defined as belonging to the same subfamily[40]. From this type of analysis it was estimated that the total repertoire of $V_H$ and $V_\kappa$ gene segments is approximately 100–300 members for each family[36,37].

Table 2 shows the percentage similarity between the ten different $V_\beta$ gene segments employed by the TB2, TB12, TB23 $V_\beta$ genes range from 85–92%, indicating they are members of the same $V_\beta$ subfamily. These $V_\beta$ gene segments have been designated $V_{\beta 8.1}$, $V_{\beta 8.2}$ and $V_{\beta 8.3}$, respectively (FIG. 1b). The similarities among the remaining $V_\beta$ gene segments ranges from 34–63%. Therefore, each of these $V_\beta$ gene segments belong to different $V_\beta$ subfamilies.

over can be significant, even higher than the rate of random single-nucleotide mutations. For example, one group of mouse H-2K variants arise by gene conversion with a frequency of $2.2 \times 1^{-4}$/locus/gamete relative to the typical mutation rate of $\sim 10^{-5}$–$10^{-6}$/locus/gamete[43]. Homologous but unequal crossing over results in the periodic expansion and contraction of multigene families, thereby favoring the coincidental evolution of these families through founder effects[44]. Since

TABLE 2
A HOMOLOGY MATRIX OF THE TEN $V_\beta$ GENE SEGMENTS.

|  | $V_{\beta 8.1}$ | $V_{\beta 8.2}$ | $V_{\beta 8.3}$ | $V_{\beta 6}$ | $V_{\beta 7}$ | $V_{\beta 1}$ | $V_{\beta 3}$ | $V_{\beta 4}$ | $V_{\beta 2}$ | $V_{\beta 5}$ |
|---|---|---|---|---|---|---|---|---|---|---|
| $V_{\beta 8.1}$+ | — | 90++ | 77 | 47 | 52 | 29 | 26 | 28 | 27 | 29 |
| $V_{\beta 8.2}$ | 92 | — | 81 | 45 | 52 | 29 | 24 | 28 | 26 | 26 |
| $V_{\beta 8.3}$ | 85 | 88 | — | 41 | 48 | 28 | 23 | 28 | 29 | 24 |
| $V_{\beta 6}$ | 55 | 54 | 54 | — | 43 | 27 | 27 | 29 | 25 | 22 |
| $V_{\beta 7}$ | 61 | 63 | 60 | 53 | — | 28 | 23 | 27 | 23 | 29 |
| $V_{\beta 1}$ | 45 | 43 | 44 | 45 | 49 | — | 33 | 53 | 20 | 37 |
| $V_{\beta 3}$ | 46 | 47 | 47 | 46 | 48 | 50 | — | 30 | 18 | 37 |
| $V_{\beta 4}$ | 46 | 46 | 46 | 47 | 47 | 62 | 50 | — | 20 | 33 |
| $V_{\beta 2}$ | 42 | 44 | 42 | 39 | 39 | 34 | 38 | 38 | — | 18 |
| $V_{\beta 5}$ | 45 | 46 | 43 | 41 | 48 | 53 | 54 | 47 | 38 | — |

+$V_{\beta n}$ denotes the subfamily.
++The numbers above the diagonal designate the % similarity of sequences on the X and Y axes when compared at the protein level while those figures below the diagonal are for % similarity at the DNA level.

In order to determine the size of the different $V_\beta$ subfamilies, Southern blot analysis was performed on mouse liver DNA using DNA probes for the $V_{\beta 1}$, $V_{\beta 2}$, $V_{\beta 4}$, $V_{\beta 5}$ and $V_{\beta 8}$ subfamilies (FIG. 2). Three of the V probes show a single band, indicating that each $V_\beta$ gene segment represents a different single-gene segment subfamily ($V_{\beta 1}$, $V_{\beta 2}$ and $V_{\beta 4}$). The $V_{\beta 5}$ and $V_{\beta 8}$ subfamilies appear to have two and three members, respectively (FIG. 2). Because the $V_\beta$ gene segment used by the TB21 V gene is the first isolated member of the $V_\beta$ subfamily, we have denoted it $V_{\beta 5.1}$ (FIG. 1b). It has been previously reported that the $V_{\beta 1}$, $V_{\beta 2}$, $V_{\beta 3}$, $V_{\beta 6}$ and $V_{\beta 7}$ subfamilies are single genes[6,31-34]. Thus, six different $v_\beta$ subfamilies with one member, one $V_\beta$ gene segment subfamily with two members and one $V_\beta$ subfamily with three members have been identified. Including the additional $V_\beta$ gene segment characterized by Malissen, et al. (in preparation), there are at least 12 $V_\beta$ gene segments in the mouse. This minimum estimate for the size of the $V_\beta$ gene segment family falls within the range indicated by the statistical analysis presented above and is consistent with the hypothesis that the $V_\beta$ gene segment repertoire is small.

The $V_\beta$ gene segment family with its six single-member subfamilies differs from those of the immunoglobulin $V_H$ and $V_\kappa$ gene families, where each contain 5 or more subfamilies with 2-40 or more members[35,37]. Southern blots of DNAs from several rodent species as well as rabbit and human analyzed with various $V_\beta$ probes indicate that the single-member $V_\beta$ subfamily sequences have diverged more rapidly than the members of at least one $V_H$ subfamily[33]. It was suggested that this reflected a need for greater polymorphism in $V_\beta$ gene segments relative to immunoglobulin V gene segments in order to accommodate both antigen and MHC recognition[33]. An alternative explanation, that we favor, for this apparently rapid divergence of single-member $V_\beta$ subfamilies involves the inability of single-copy genes to participate in the generally conservative gene correction mechanisms such as gene conversion and homologous but unequal crossover[41,42]. The rate of these mechanisms is affected by the degree of similarity between participating sequences. Hence, in multigene families, the rate of gene conversion and unequal crossover tend to favor the maintenance of similar sequences within families, these mechanisms can play a significant role in reducing the rate of divergence of gene families relative to that of single-copy genes. Consistent with this view is the observation that the three-member $V_{\beta 8}$ subfamily is more highly conserved than the single-member $V_\beta$ subfamilies, is as conserved as the T15 $V_H$ subfamily, and varies in size among several mammalian species[33]. In addition, the rate of divergence among the members of the $V_{\beta 8}$ subfamily, based upon the ratio of amino acid replacement to silent-nucleotide substitutions, has been calculated (data not shown) and is similar to that calculated for members of the T15 $V_H$ subfamily (G. Slu, unpublished observation). We conclude, therefore, that the apparent rapid divergence of single-member $V_\beta$ subfamilies is most likely a consequence of their inaccessibility to the homogenizing effects of gene conversion and unequal crossover, and not due to selection for an increased mutation rate. It is unclear why single-member subfamilies appear to have arisen exclusively in the $V_\beta$ family. In this regard it is also interesting to note that no $V_\beta$ pseudogenes have been found, whereas at least 30% of $V_H$ gene segments are pseudogenes[36]. These observations raise the question of what mechanisms are responsible for retarding the duplicative processes seen in other V gene families.

The $V_\beta$ gene family employs a variety of mechanisms for diversification—some similar and others distinct from those in the immunoglobulin gene families.

Despite the fact that a limited number of $V_\beta$ gene segments have been identified, all 15 of the $V_{62}$ gene sequences examined are distinct from one another due to combinatorial and somatic mutational mechanisms (FIG. 1a)[6,31-34]. The germline, combinatorial and somatic mutation contributions to $V_\beta$ gene assembly are summarized below.

Germline.

The $\beta$ gene family differs from its $V_H$ counterpart in the apparently limited number of germline $V_\beta$ and $D_\beta$ gene segments. First, the expressed $V_\beta$ gene segment repertoire appears to consist of 21 or fewer members, whereas the heavy chain repertoire contains 100–300 germline $V_H$ gene segments of which at least 30% are pseudogenes[36]. Second, although we do not know the number of germline $D_\beta$ gene segments, all of the D segments found in rearranged $V_\beta$ genes can be derived from the two $D_\beta$ gene segments previously identified assuming that junctional flexibility and N-region diversification is sufficiently extensive in some cases to leave only three nucleotides of the original germline $D_\beta$ gene segment (FIG. 3). Deletion of as much as the entire germline D segment has been observed in $V_H$ gene assembly (F. Alt, personal communication). Hence there appears to be a small number of $D_\beta$ gene segments, possibly just two, while the heavy chain locus has at least 10-20 $D_H$ segments[45]. Finally, there are 12 apparently functional $J_\beta$ gene segments, six in each $J_\beta$ gene cluster[6,8,9]. The $V_H$ genes have four $J_H$ gene segments[16, 46,47].

Combinatorial.

Combinatorial joining permits either $D_\beta$ gene segment to be joined to any downstream $J_\beta$ gene segment (six $D_{\beta1}J_{\beta1}$+six $D_{\beta1}J_{\beta2}$+6$D_{\beta2}J_{\beta2}$=18 $D_\beta$-$J_\beta$ rearrangements). Individual $V_\beta$ segments appear to join any $D_\beta$-$J_\beta$ rearrangements (21×18=378 $V_\beta$ genes). The $D_{\beta1}$ and $D_{\beta2}$ sequences are each used aproximately half the time in the sample analyzed and $D_{\beta1}$-$J_{\beta2}$ joinings occur as frequently as $D_{\beta1}$-$J_{\beta1}$ joinings (3 vs. 3)(Table 1). Eight different $J_{\beta1}$ and $J_{\beta2}$ gene segments are used, with $J_\beta$ gene segments being employed in 11 out of 14 examples. Thus one would expect individual V gene segments to join with the $J_{\beta1}$ gene cluster 25% of the time and the $J_{\beta2}$ gene cluster 75% of the time and this is what is seen—thus supporting the contention that $D_\beta$-$J_\beta$ joining occurs randomly. However, the $J_{\beta2.5}$ gene segment is employed six of the 11 times that the $J_{\beta2}$ cluster is employed. Whether this bias for the $J_{\beta2.5}$ gene segments represents the selective effects of antigen or the mechanisms involved in the DNA rearrangement process is uncertain.

There may be two additional mechanisms. Asymmetric recognition sequences surrounding the D gene segments potentially permit $V_\beta$-$J_\beta$ and $D_\beta$-$D_\beta$ joinings[10-12]. Data consistent with the former possibility have been presented,[48] although the interpretation of these data are difficult due to the possible loss of D gene sequences during $V_\beta$ gene segment rearrangement. As yet there is no evidence for either mechanism, hence if these joinings do occur, they would appear to be infrequent.

Somatic Mutation.

Junctional flexibility in joining gene segments is illustrated in FIGS. 1a and 3. Extra nucleotides ranging in number from one to six are found at either end of the D gene segments. Interestingly, there appears to be no G/C bias (50%) in this N-region diversification in contrast to that reported for immunoglobulin N-region diversity[22].

Figure 4:
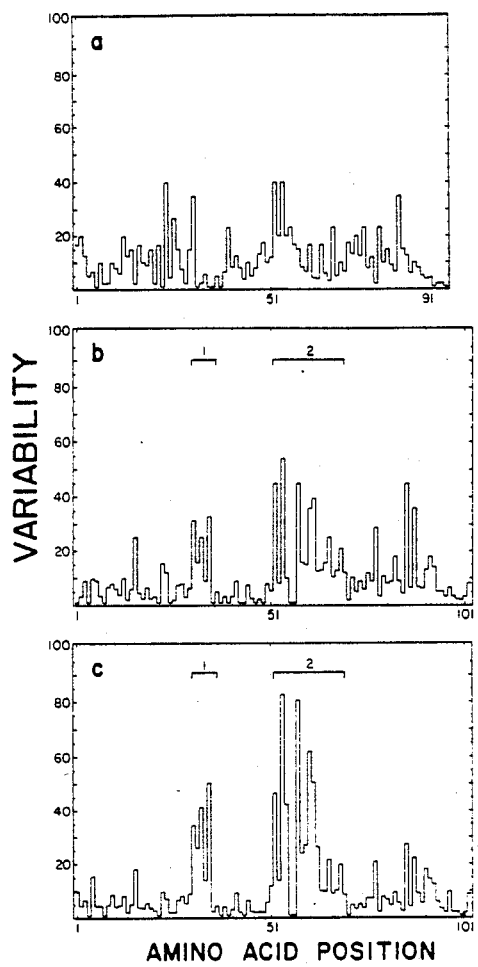

There is a special somatic mutational mechanism seen only in T cells[34]. The $D_\beta$ gene segments may join to the $V_\beta$ gene segments in all three translational reading frames, with the only requirement being that the $D_\beta$-$D_\beta$ and $V_\beta$-$D_\beta$ joinings leave the $J_\beta$ sequence in an open reading frame (FIG. 4). In contrast, examination of about 60 published and unpublished $V_H$ genes indicate that $D_H$ gene segments can only be joined in one translational reading frame (ref. 34 and T. Hunkapiller, unpublished observation). This observation was also noted for the $V_H$ genes involved in the immune response to arsonate[49]. The use of all three $D_\beta$ translational reading frames in principle increases threefold the diversity possible by $V_\beta$-$D_\beta$ joining.

The somatic hypermutation of immunoglobulin genes occurs late in B-cell development, perhaps upon exposure to antigen[50]. It has been noted that the germline $V_{\beta3}$ gene segment is identical to the 2B4 $V_\beta$ gene segment, derived from a $T_H$ cell specific for cytochrome C[6] and to the 3H.25 $V_\beta$ gene segment, derived from a $T_H$ cell specific for hen egg lysozyme[34]. Thus, there was no evidence for somatic hypermutation of $V_\beta$ gene segments in the two examples that have been studied. In contrast, it was recently reported that somatic variants can arise in alloreactive T cells in vitro[51], although the physiological relevance of this observation is uncertain. We see two nucleotide substitutions among the three $V_{\beta1}$ and two nucleotide substitutions between the two $V_{\beta2}$ gene segments that have been sequenced (FIG. 1a)[31,33]. There is a single silent nucleotide substitution between the 86T1 $V_{\beta1}$ and the 1.9.2 and BW5147 $V_{\beta.1}$ gene segments and a single amino acid replacement substitution between the BW5147 $V_\beta$ gene segment and the 86T1 and 1.9.2 $V_\beta$ gene segment (FIGS. 1a and 1b)[31]. Since all three of these $V_\beta$ sequences are derived from different strains of mice (Table 1), these differences may come from strain polymorphism. On the other hand, the nucleotide substitutions between Ar1 $V_{\beta2}$ and E1 $V_{\beta2}$ sequences, one silent and one replacement substitution (FIGS. 1a and 1b)[33], could be due to strain polymorphism (Table 1) or somatic hypermutation. Characterization of the germline $V_{\beta1}$ and $V_{\beta2}$ gene segments from the different mouse strains will clarify this issue. There are no other differences between the repeatedly expressed $V_{\beta3}$ and $V_{\beta8.1}$ gene segments (FIGS. 1a and 1b). Furthermore, the associated $J_\beta$ gene segments do not have any nucleotide substitutions, outside the probable N-regions, that might be explained by somatic hypermutation. Had a comparable sample analysis been carried out on $V_H$ or $V_\beta$ genes, examples of somatic hypermutation would have been seen. Thus we tentatively conclude that the rate of somatic hypermutation, if it exists under normal physiological conditions, is much lower in $V_\beta$ than in immunoglobulin V genes.

$\beta$ chain V regions are structurally similar to immunoglobulin V regions $V_\beta$ genes are similar to immunoglobulin V genes in their gene organization and in many of their strategies for diversification, but appear to differ from immunoglobulins in their V gene segment repertoire, V gene segment subfamily organization, and relative use of somatic hypermutation. We were interested in determining the extent that these similarities and differences are reflected in the protein structure of the $V_\beta$ gene segments and their immunoglobulin counterparts.

The percentage similarities, at the protein level (Table 2), between the different $V_\beta$ subfamilies ranges from 18–53% and 77–90% between members of the $V_{\beta8}$ subfamily. Although this range extends to a lower value (18%) than that observed so far for mouse $V_H$ segments (34%), it is close to the lowest values observed between known human $V_H$ segments (24%) (data not shown). As discussed below, the set of human $V_H$ gene segments is probably a more representative sampling of the total $V_H$ family than mouse $V_H$ segments. Thus the total variation between different $V_\beta$ segments can be extensive (82%) but not significantly larger than the variation found between immunoglobulin V subfamilies (76%).

Another informative means of analyzing sequence variation within the $V_{\beta 2}$ gene segment family is to determine the distribution of the variation between V segments. Kabat and Wu analyzed this distribution among immunoglobulin V regions by measuring and plotting a parameter termed variability at each amino acid position[52]. From this analysis, it was concluded that variability was not distributed uniformly. Rather, there were three regions found to have a relative "hypervariability"[52]. These regions, covering aproximately one third of the V sequences, have been termed hypervariable regions and have been shown to form the antigen-binding crevice of antibody molecules[53-55]. Two of these hypervariable regions are encoded by the V gene segments and the third is found in the $V_H$-$D_H$-$J_H$ or $V_L$-$J_L$ junction regions[56]. We have performed a similar variability analysis with the 10 translated mouse $V_\beta$ gene segments (FIG. 1b). The result was compared to variability plots of the set of total human $V_H$ segments and a set of 18 human $V_H$ segments with blocked $\alpha$ amino groups (FIG. 5). Human $V_H$ segments were chosen for comparison because they offer a more random representation of $V_H$ sequences than any set of mouse V segments that have been sequenced. This is because mouse $V_H$ sequences have been highly selected in comparison with $V_\beta$ sequences in two ways. First, mouse $V_H$ sequences are derived mostly from immunoglobulins that recognize a relatively limited number of antigens Second, for technical reasons mouse $V_H$ sequences are almost exclusively determined from heavy chains with unblocked $\alpha$ amino groups despite the fact that 80% of mouse serum immunoglobulins have heavy chains with blocked $\alpha$ amino groups[57]. The blocked human $V_H$ sequences, on the other hand, were then selected randomly from a variety of tumors and patients with other pathological conditions[56]. We have found that the variability distribution of the mouse $V_\beta$ segments (FIG. 5a) is remarkably similar to the distribution found for the set of human $\alpha$ amino blocked $V_H$ segments (FIG. 5b). The variability distribution of the total set of human $V_H$ segments (FIG. 5C) represents a less random sampling than the human $\alpha$ amino blocked $V_H$ segments for the same reasons given for the mouse sequences, and shows a more accentuated variability at the two classically defined hypervariable regions. The total set of human $V_H$ sequences also exhibits a slightly lower background variability, due in part to the larger size of the sampling. Thus when sample size and selection is considered, we conclude that the variability distributions in the $V_\beta$ and segments are not significantly different from one another. We also find it difficult to argue that $V_\beta$ regions have novel hypervariable regions relative to immunoglobulin V regions, as suggested previously[33].

We also have compared $V_\beta$ and immunoglobulin V segments by analyzing them for two properties believed to reflect important structural features of these molecules, the distribution of a $V\beta$-pleated sheet forming potential[58] and the predicted hydrophobicity profile[59]. We find the results of these analyses to be virtually the same for mouse $V\beta$, $V_H$ and $V_K$ segments (FIG. 6) An additional peak in the $V_H$ and $V_K\beta$-pleated sheet plots not seen in the $V_\beta$ plot is an artifact due to length variation of different $V_H$ and $V_K$ segments in this region. $V_\beta$ sequences also conserve essentially the same group of residues that in immunoglobulins are thought to be important in intra-chain structural interactions (data not shown).

These results strongly support the contention that the general biochemical characteristics and predicted secondary structures of the $V_\beta$, $V_H$, and $V_K$ regions are similar to one another. Accordingly, we predict that the T-cell receptor and immunoglobulin molecules probably fold into similar tertiary structures. Therefore, from the analysis of the sequence variability and structural predictions, we find no evidence for the existence of any fundamental differences in how $V_\beta$ gene segments can contribute to determinant recognition when compared to immunoglobulin V gene segments. This conclusion is supported by the observation that MHC-restricted antibodies have been raised to influenza antigens[60]. This observation implies that there need be nothing structurally unique about the T-cell receptor structure and its ability to recognize antigen and MHC restricting elements.

The implications of $V_\beta$ gene structure and repertoire to antigen/MHC specificity T cells are capable of recognizing a similar set of antigens recognized by B cells in conjunction with the entire range of polymorphic MHC molecules found in a species. Therefore, the T-cell receptor repertoire is expected to be at least equal to the immunoglobulin repertoire. Our observations suggest that the $\beta$ chain genes employ a limited number of $V_\beta$ gene segments and that somatic hypermutation is infrequent or even nonexistent. However, there are several reasons why the $V_\beta$ gene repertoire may not be significantly different from that of immunoglobulin V genes. First, although there may be few $V_\beta$ gene segments, they are generally distributed as separate subfamilies. These $V_\beta$ subfamilies exhibit the same overall range of sequence diversity as different $V_H$ subfamilies.

Second, the number of $V_\beta$ gene segments may be one-tenth to one-third the number of $V_H$ or $V_K$ gene segments, but at least 30% of the $V_H$ and $V_K$ gene segments are pseudogenes.[36] Also, the number of $J_K$ gene segments is three times the number of $J_H$ or $J_K$ gene segments and the translational capacity of the $D_\beta$ and $D_H$ gene segments appear similar. Third, the principal role of somatic hypermutation in immunoglobulin V genes may be to increase the antigen-binding affinity of antibodies rather than to generate a broader range of antigen recognition[51,61]. Fourth, chains and immunoglobulins both employ junctional flexibility and N-region diversification which are major contributors to the generation of diversity within a specific region of the molecule involved in determinant recognition. Hence, we conclude that limited number of expressed $V_\beta$ gene segments and the infrequent use of somatic hypermutation suggested by our observations does not necessarily reflect a restricted $\beta$ chain repertoire. Rather, these observations do imply that $\beta$ chain somatiic diversification is more focused to the 3' portion of the $V_\beta$ gene.

There are two possible explanations for the apparent low frequency of somatic hypermutation of $V_\beta$ genes. First, somatic hypermutation in B cells is primarily associated with immunoglobulin class switching and occurs late in B cell differentiation[23]. The role of somatic hypermutation at this time may be primarily to increase the binding affinity of the antibody to the particular stimulating antigen. T-cell receptors may operate with a lower binding affinity due either to a lower affinity requirement for T-cell response or the stabilizing effect of accessory molecules on the T-cell surface. Consequently, T cells simply may not benefit from the additional somatic variation provided by somatic hypermutation. Second, somatic hypermutation may be selected against in T cells. In B cells somatic hypermutation occurs late in development, after antigen stimulation. It is possible that somatic hypermutation does not occur late in T-cell development, after immunocompetent cells have migrated from the thymus, in order to prevent the generation of autoreactive regulatory or cytotoxic T cells in the periphery. Thus somatic diversification may be restricted to occur early in T-cell development which allows the thymus to remove autoreactive cells arising from the somatic variation. B cells may not be so restricted because of the strong influence of regulatory T cells[62], and thus are free to undergo somatic hypermutation later in B-lymphocyte development in response to antigen stimulation.

As Table 1 demonstrates, there is no simple correlation between a particular $V_\beta$ gene segment and distinct antigen specificities or MHC restricting elements. For example, the $V_{\beta 2}$ gene segment is used by a $T_H$ cell specific for TNP and the I-A$^d$ MHC molecule (E1) and a TC. specific for the H-2D$^d$ alloantigen (AR1). If the $V_\beta$ and $V_\alpha$ regions fold in a manner similar to their immunoglobulin counterparts as is suggested for $V_\beta$ regions by our earlier analysis, then both chains will play a critical role in generating the binding site for antigen plus MHC. Accordingly, there is no reason to believe that either chain will have a particular role in recognizing either antigen or MHC individually.

REFERENCES

1. Allison, J. P., McIntyre, B & Bloch, D. J. Immunol., 129, 2293-2300 (1982).
2. Haskins, K., Kubo, R., White, J., Pigeon, M., Kappler J. & Marrack, P. J. Exp. Med., 157, 1149-1169 (1983).
3. Meuer, S. C., Fitzgerald, K A., Hussey, R. E., Hodgdon, J. C., Schlossman, S. F. & Reinherz, E. L. J. Exp. Med., 157, 703-719 (1983).
4. Caccia, N., Kronenberg, N., Saxe, D., Haars, R., Bruns, G., Goverman, J., Malissen, M., Willard, H., Yoshikai, Y, Simon, M., Hood, L. & Mak, T. Cell, 37, 1091-1099 (1984).
5. Lee. N. E., D'Eustachio. P., Pravtcheva, D., Ruddle, F. H., Hedrick, S. M. & Davis, M. M. J. Exp. Med., 160, 905-913 (1984).
6. Chien, Y.-H., Gascoigne, N. R. J., Kavaler, J., Lee, N. E. & Davis, M. M. Nature, 309, 322-326 (1984).
7. Siu, G., Clark, S., Yoshikai, Y., Malissen, M., Yanagi, Y., Strauss, E., Mak, T. & Hood, L. Cell, 37, 393-401 (1984).
8. Malissen, M. Minard, K., Mjolsness, S., Kronenberg, M., Goverman, J., Hunkapiller, T., Prystowsky, M., Yoshikai, Y., Fitch, F., Mak, T & Hood, L. Cell, 37, 1101-1110 (1984).
9. Gascoigne, N. R. J., Chien, Y.-H , Becker, D. M., Kavaler, J. & Davis, M. M., Nature, 310, 387-391 (1984).
10. Kavaleerr, J., Davis, M. M. & Chien Y.-H., Nature, 310, 421-423 (1984).
11. Siu, G., Kronenberg, M., Strauss, E., Haars, R., Mak. T. W. & Hood, L., Nature, 311, 344-349 (1984).
12. Clark, S. P., Yoshikai, Y., Taylor, S., Siu, G., Hood, L. & Mak, T. W., Nature, 311, 387-389 (1984).
13 Brack, C., Hirama, M., Lenhard-Schuller, R. & Tonegawa, S., Cell, 13, 1-14 (1978).
14. Seidman, J., Max, E. & Leder, P., Nature, 280, 370-375 (1979).
15. Sakano, H., Huppi, K., Heinrich, G. & Tonegawa, S., Nature, 280, 288-294 (1979).
16. Early, P., Huang, H., Davis, M., Calame, K. & Hood, L., Cell, 19, 981-992 (1980).
17. Sakano, H., Maki, R., Kurosawa, Y., Roeder, W & Tonegawa, S., Nature, 286, 676-683 (1980).
18. Schilling, J., Clevinger, B., Davie, J. M. & Hood, L., Nature, 283, 35-40 (1980).
19. Weigert, M., Perry, R., Kelley, D., Hunkpiller, T., Schilling, J. & Hood, L., Nature, 283, 497-499 (1980).
20. Sakano, H., Kurosawa, Y., Weigert, M. & Tonegawa, S., Nature, 290, 562-565 (1981).
21. Kurosawa, Y., Von Boehmer, H., Haas, W., Sakano, H., Trauneker, A. & Tonegawa, S., Nature, 290, 565-570 (1981).
22. Alt, F. & Baltimore, D., Proc. Natn. Acad. Sci. USA, 79, 4118-4122 (1982)
23. Kim, S., Davis, M., Sinn, E., Patten, P. & Hood, L., Cell, 27, 573-581 (1981).
24. Tonegawa, S., Nature, 302, 575-581 (1983).
25. Golub, E. , Cell, 21, 603-604 (1980).
26. Matzinger, P & Zamoyska, R., Nature, 297, 628 (1982).
27. Doherty, P. C. & Zinkernagel, R. M., J. Exp. Med., 141, 502-507 (1975)
28. Thomas, D. W., Yamashita, U. & Shevach, E. M., J. Immunol., 119, 223-226 (1977) .
29. Germain, R. N. & Benacerraf, B. Scand, J. Immunol. 13, 1-10 (1981).
30. Zinkernagel, R. M. & Doherty, P. C., Adv. Immunol., 27, 51-177 (1979).
31. Hedrick, S. M., Nielsen, E. A., Kavaleeer, J., Cohen, D. I. & Davis, M.M., Nature, 308, 153-158 (1984).
32. Saito, H., Kranz, D. M., Takagaki, Y., Hayday, A. C., Eisen, H. N. & Tonegawa, S., Nature, 309, 757-762 (1984).
33. Patten, P., Yokota, T., Rothbard, J., Chien, Y.-H., Arai, K. & Davis, M. M., Nature, 312, 40-46 (1984) .
34. Goverman, J., Minard, K., Shastri, N., Hunkapiller, T., Hansburg, D., Sercarz, E. & Hood, L., Cell, in press.
35. Scollay, R. G., Butcher, E. C. & Weissman, I. L., Eur. J. Immunol. 10, 210-218, (1980).
36. Brodeur, P. H. & Riblet, R., Eur. J. Immunol. 14, 922-930 (1984)
37. Cory. S., Tyler, B. M. & Adams, J. M., J. Mol. Appl. Genet., 1, 103-116 (1981).
38. Hedrick, S. M., et al., Pro. Natl. Acad. Sci. USA, 82, 531-535 (1985).
39. Kronenberg, M., et al., Nature, 313, 647-653 (1985).
40. Crews, S., Griffin, J., Huang, H., Calame, K. & Hood, L., Cell, 25, 59-66 (1981).
41. Baltimore, D., Cell, 24, 592, 594 (1981).
42. Smith, G. P., Science, 191, 528-535 (1976).
43. Klein, J. Adv. Immunol., 26, 55-146 (1978).
44. Hood, L., Campbell. J. H. & Elgin, S. C. R., Ann. Rev. Genet., 9, 305-353 (1975).
45. Kurosawa, Y & Tonegawa, S. J., Exp. Med., 155, 201-218 (1982).
46. Bernard, O. & Gough, N. M., Proc. Natn. Acad. Sci. USA, 77, 3630-3634 (1980).
47. Gough, N. M. & Bernard, O., Proc. Natn. Acad. Sci. USA, 78, 509-513 (1981).
48. Yoshikai, Y., Anatoniou, D., Clark, S. P., Yanagi, Y., Sangster, R., Van den Elsen, P., Terhorst, C. & Mak, T. W., Nature, 312, 521-524 (1984).
49. Manser, T., Huang, S.-Y. & Gefter, M. L., Science, 226, 1283-1288 (1984).

50. Griffith, G. M., Berek, C., Kaartinen, M. & Milstein, C., Nature, 312, 271–275 (1984).
51. Augustin, A. A. & Sim, G. K., Cell, 39, 5–12 (1984).
52. Wu, T. T. & Kabat, E. A., J. Exp. Med., 132, 211–250 (1970).
53. Amzel, L. M. & Poljak, R. J., Ann. Rev. Biochem., 48, 961–997 (1979).
54. Davies, D. R. & Metzger, H., Ann. Rev. Immunol., 1, 87–117 (1983).
55. Amit, A. G., Mariuzza, R. A., Phillips, S. E. V. & Poljak, R. J., Nature, 313, 156–158 (1985).
56. Kabat, E. A., Wu, T. T., Bilofsky, H., Reid-Miller, M., & Perry, H., Sequences of Immunological Interest (U.S. Department of Health and Human Services, Washington, D.C. 1983)
57. Capra, J. D., Wasserman, R. L. & Kehoe, J. M., J. Exp. Med., 138, 410–427 (1973).
58. Chou, P. & Fassman, G., Ann. Rev. Biochem., 47, 251–276 (1978).
59. Kyte, J. & Doolittle, R. F., J. Mol. Biol. 157, 105–132 (1982).
60. Wylie, D. E., Sherman, L. A. & Klinman, N. R. J. Exp. Med., 155, 403–414 (1982).
61. Rodwell, J., Gearhart, P. & Karush, F., J. Immunol., 130, 313–316 (1983).
62. Mitchell, G. F. & Miller, J. F. A. P., J. Exp. Med., 128, 821–837 (1968).
63. Huynh, T. V., Young, R. A. & Davis, R. W. in DNA Cloning: A Practical Approach (ed. D. Glover) (IRL Press, Oxford, 1984).
64. Sanger, F., Nicklen, S. & Coulsen, A., Proc. Natn. Acad. Sci. USA, 74, 5463–5467 (1977).

SECOND SERIES OF EXPERIMENTS

HTLV-I is associated with an extremely malignant form of human T cell lymphoma, that of a helper phenotype (Leu 3/T4 and Leu 3/T3 expressing). Previous results with the retrovirus HTLV-I have demonstrated that the virus binds to both HTLV and non HTLV-associated T cell lymphoma and leukemia, it was desired to determine the cellular binding site for this virus. FIG. 6 demonstrates a rhodamine-labeled virus preparation of HTLV-I binding to the T-lymphoma cell line Jurkat, with a decreased fluorescence noted after a 1:1 cold virus inhibition. These curves represent a FACS analysis of virus bound per cell compared with background fluorescence. It has previously been demonstrated that this binding is characteristic of only transformed T lymphocytes, as an in vitro T cell line (G11) even though producing HTLV-I virions, and peripheral blood lymphocytes, did not show a substantial amount of labeled virus binding. Therefore, in the majority of T cell lines so far tested, virus binding appears to be transformation-specific. The lines tested to date include T cell ALL, CEM-CCRF, 8402, Jurkat, HPB-ALL, the in vitro HTLV-I expressing cell lines which include HUT-102, Gann, and the in vitro transformed T cell lines MT-2 and C92PL. To date, the only T cell lymphomas which do not express HTLV-I receptors are HUT-78, a mycosis fungoides cell line and MOLT-4. [See McGrath, M. S. and Weissman, I. L, Human T-cell Leukemia Lymphoma Viruses, Cold Spring Harbor Laboratory, p. 205–215 (1984)].

To test whether known T cell differentiation antigens might be involved in the binding of HTLV-I, a series of monoclonal antibodies have been tested for the ability to block virus binding to MT-2 cells. The results obtained demonstrated that HTLV binding was not inhibited by a series of antibodies directed to T cell differentition markers including anti-Leu-1, 2, 3, 4 and anti-HLA-DR framework antibodies as well as antibodies to the IL-2 receptor TAC. More recently, it has been shown that murine leukemia virus (MuLV) binding to a specific MuLV-induced T cell lymphoma is at or near the T cell antigen receptor. The evidence supporting this conclusion is that a clonotypic antibody directed against the T cell receptor on this lymphoma, C6VL-1, completely inhibits virus binding to the lymphoma, and the binding of this antibody also leads to a blockade of lymphoma cell proliferation. These results are consistent with the previously proposed receptor-mediated leukemogenesis hypothesis. [McGrath. M. S. and Weissman, I. L., Cold Cpring Harbor Conf. Cell Proliferation 5 577(1978); McGrath, M. S. and Weissman, I. L., Cell 17:65(1979)].

The $V_\beta$ chain of the T cell antigen receptor from the T cell lymphoma, MOLT-3, has been cloned and its DNA sequence determined [Yagita et al, Nature 308:14.5 (1984)]. From this sequence the amino acid sequence has been deduced. Both the amino acid sequence of the variable region of the $\beta$ chain and the DNA which encodes it have been identified. Based upon this knowledge of the amino acid sequence of the variable region a 22 amino acid peptide (M3V) identical to the 22 amino acids located at the N-terminus of the variable region has been prepared using known method. This peptide has the following sequence:

Gly-Val-Ile-Gln-Ser-Pro-Arg-His-Glu-Val-Thr-Glu-Met-Gly-Gln-Glu-Val-Thr-Leu-Arg-Cys.

The M3V peptide was coupled to KLH, precipitated in alum, and injected into Lewis rats intraperitoneally once a week for 3 weeks. Just prior to the third injection, 3 rats were bled and the antiserum was harvested and checked for binding activity to ovalbumin coupled M3V peptides. A titration curve of rat antiserum binding activity to plate-bound M3V ovalbumin demonstrated that the rat antiserum had antipeptide activity which could be titrated out to greater than 1:2,500. Antiserum derived from one of the rats bound significantly to the T cell ALL, Jurkat cell line, in contrast with non-immune rat antiserum which did not. This indirect immunofluorescence analysis was carried out on the previously mentioned series of T cell neoplasms, many of which each reacted significantly with the anti-M3V antiserum. This antiserum stained only a minor subpopulation of peripheral blood lymphocytes as well as human thymocytes. Upon several sequential analyses (N=15) it has been found that only approximately 0.5-% of thymocytes or peripheral blood lymphocytes are recognized by the M3V rat antiserum.

To determine whether the anti-M3V antiserum was directed against a native beta chain T cell receptor molecule, the JM (Jurkat) lymphoma was cell surface $^{125}$I-labeled, and immunoprecipitated. A characteristic 40–45,000 molecular weight molecule was recognized on the surface of this T cell lymphoma, by the anti-M3V antiserum which was specifically competed for by free M3V-peptide. Under non-reducing conditions, a molecular complex of approximately 85,000 molecular weight is recognized on the surface of this T cell lymphoma by this antiserum, which again is characteristic of the alpha-beta chain T cell receptor complex.

To determine whether the molecule recognized by the anti-M3V antiserum mediated binding of HTLV-I to T cell lymphomas, a test was carried out to determine whether preincubation of cells with this antiserum would block virus binding. FIG. 7 demonstrates that preincubation of the Jurkat T cell ALL cell line with anti-M3V antibodies significantly inhibited virus binding, to a much greater extent than a saturating amount of HTLV-I virus, a characteristic not shared with any other monoclonal antibody. In several experiments, anti-Leu-4 has been shown to block virus binding to a minor degree. This experiment has been repeated with several of the previously mentioned HTLV-I binding lymphomas (8402, CEM, MT-2, C91PL, JM), and consistently similar results have been obtained, indicating that not only does HTLV-I bind to the majority of human T cell malignancies tested to date, but that these lymphomas share an antigenic crossreactivity detected by an antiserum directed against a T cell receptor beta chain peptide.

THIRD SERIES OF EXPERIMENTS

Hybridomas (between immune rat spleen cells and the mouse nonsecretor myeloma 8653) producing monoclonal antibodies specific for the M3V peptide have also been prepared using well known methods [Galfre, G., et al., Nature, (1977)]. These hybridomas have been screened using immunoprecipitation to identify those which produce antibodies specific for the M3V peptide. One such hybridoma designated clone 43 has been identified.

This hybridoma, and more specifically the monoclonal antibody produced by it, has been used to diagnose T cell lymphoblastic leukemia in a human patient. Thus mononuclear cells, prepared by subjecting the patient's peripheral blood to Ficoll hypaque density centrifugation, were stained ($10^6$) with 100 microliters of clone 43 hybridoma culture supernatant containing monoclonal antibody against the N-terminal peptide M3V. The mixture was incubated at 4° C. and 0.1% azide for 30 minutes and washed with culture media 1640 with 5% serum. Then 100 microliters of fluorescein conjugated goat anti-rat IgG at 10 µg/ml w as added to the washed cells and incubated at 4° C. for 30 minutes. Excessive antibodies were removed by repetitive washing of the cells. The final cell suspension Was examined for antibody reactivity by passing the cells through a flowcytometer (Cytofluorograf 50H, Ortho Diagnostic Systems, N.J.).

Antibodies Leu 1, Leu 4, Leu 5, Leu 9 were purchased from Becton Dickinson and Company; OKT4 from Ortho Diagnostic Systems. Monoclonal antibody 33.11, a rat $IgG_{2a}$ served as an isotype method control for monoclonal 43.

The results are set forth in Table 3.

TABLE 3

| Monoclonal Antibody | Percent reactive cells |
|---|---|
| Leu 1 | 60% |
| 4 | 40-50% |
| 5 | 40-50% |
| 9 | 25% |
| OKT 4 | 60% |
| Clone 33 | 0.5% |
| 43 | 60-70% |

Similar analysis of lymphocytes from 15 normal donors revealed less than 0.5% of cells stained with the clone 43 antibody.

These results show that a monoclonal antibody directed to the N-terminal peptide of the variable region of the T cell receptor of a T cell lymphoma/leukemia may be used as a highly specific diagnostic reagent for human lymphoma/leukemia.

FOURTH SERIES OF EXPERIMENTS

Production of monoclonal antibodies against N-terminal peptides of the β chain of the T cell antigen receptor derived from anti-lung tumor T cell clones.

Growth and Propagation of Anti-Lung Carcinoma T Cell Clones

T cell clones reacting against lung tumor cells are isolated and established from tumor biopsy samples by using the method of Mayer et al. J.Immunol. 134: 258(1985)]. Lung tumor biopsy specimens containing T cells are cultured in medium containing interleukin-2 (IL-2) and antigen. T lymphoblasts migrate out of the tissue and increase in number. The T cell nature of isolated lymphoblasts is ascertained by T cell typing for characteristic cell surface* markers such as OKT3, OKT4 and OKT8. The clones derived from these lymphoblasts are obtained by limiting dilution [Celis, et al., J. Immunol. 132: 1511 (1984)]. The analysis of functions possessed by these cell clones is performed by antigen proliferation assay, mixed lymphocyte cultures, helper assay and for cell-mediation cytotoxicity [Mayer, et al., J. Immunol, 134: 258 (1985); and Celis, et al., J. Immunol, 132: 1511 (1984)]. Large amounts of individual T cell clones are established either by stimulating T cells with appropriate antigen, (feeding cells an IL-2 supplement as described by Mayer et al,) or by the T/T hybridoma fusion method using a drug marker T cell line [Lee et al., Proc. Natl. Acad. Sci. USA 79: 7857 (1982); and DeFreitas et al., Proc. Natl. Acad. Sci. USA 79: 6646 (1982)]. Restriction enzyme pattern analyses of somatic DNA from the clones of the T-T hybrids is used to ascertain the clonality of these T cells.

Isolation of T Cell Antigen Specific Genes from T Cell Clones.

Total cellular RNA is extracted from the T cell clones by the guanidinium isothiocyanate-cesium choride method [Maniatis T., *Molecular Cloning, A Laboratory Manual* (Cold Spring Harbor Manual, p. 196 (1982)]. mRNA can be enriched by oligo (dT)—cellulose chromatography [Aviv H. & Leder, P., PNAS 69: 1408 (1972)].

One of several methods of isolating the receptor mRNA is used depending on the abundance of the mRNA present in the T cell clones. In the case of low mRNA abundance, a cDNA library is constructed using the following steps. Double-stranded cDNAs are generated from the RNA using the reverse transcription approach described by Land et al. [Nucleic Acid Res. 9: 2251 (1982)]. DNA segments with a length between 0.5 to 2 kilobase as determined by preparative agarose gel electrophoresis are selected and inserted into a bacterial plasmid vector, such as PFP502EB5 (Clark and Mak, Nucleic Acid Res. 10: 3315 (1982); M13 phage, or pBR 322 (Maniatis et al, *Molecule Cloning, A Laboratory Manual* Cold Spring Harbor Laboratory, (1982)] using well known methods such as those described in the above manual. The cDNA library is created by transfecting *E. coli* strain HB 101. Independent clones containing a full spectrum of the cDNA are obtained and stored. Alternatively, the cDNA library is made only after subtracting the T cell cDNA with mRNA from a human B cell line HSC-[58] [Hedrick et al., Nature 308: 148 (1984)]. To screen for cDNA clones of mRNA encoding the alpha and beta chain of T cell antigen receptors in the T cell clone, radiolabeled DNA probes corresponding to the alpha and beta chain constant domain of the T cell receptor in Jurkat or Molt-3 human T cell lines are reacted with replicas of the transfected bacteria in the cDNA library. Positive bacteria clones are picked and plasmid DNA extracted for subsequent DNA determination. [Yanagi et al., Nature 308: 145 (1984)].

Deducing Amino Acid Sequence of the Receptor Genes

The nucleotide sequence of the cDNA encoding the receptor genes is determined using the chain terminating inhibitor method of Sanger et al [Proc. Nat'l. Acad. Sci. 74: 5463 (1977)] or the method of Maxam and Gilbert [Meth. Enzym. 65: 499 (1980)]. The amino acid sequence of the V, J and D domains of the alpha and beta polypeptides is determined [Yanagi et al., Nature 308: 145 (1984); and Chien et al., Nature 312: 31 (1984)].

In the case of high mRNA abundance in the T cell clone, the following method is used. The nucleotide sequence of the variable region of the alpha or beta gene mRNA is determined by the primer extension method [Koartinen et al., J. Immunol. 130: 937 (1983)]. A purified, small fragment of labelled T cell receptor gene DNA is mixed with either enriched mRNA or total cellular RNA and denatured at 80° C. in buffer containing formamide, NaCl, EDTA and Hepes. After hybridization at lower temperature, DNA-RNA hybrids are purified by precipitation with ethanol and dissolved in Tris buffer. Reverse transcriptase and deoxyribonucleotides are added to the DNA-RNA hybrids. After incubation, the extension product is purified by ethanol precipitation and the sequence analyzed on sequencing gels.

Synthesis of Receptor Peptides

Peptides corresponding to the N-terminus of the V, J and D sequences of the receptor are synthesized by the Merrifield solid-phase method. [Marglin and Merfifield, Ann. Rev. Biochem. 39: 841 (1970); Merrifield, J., Amer. Chem. Soc. 85: 2149 (1963)]. A cysteine residue is added to the amino- or carboxyterminus of the peptides to allow coupling to a protein carrier. The peptides are then purified by HPLC.

Production of Antisera and Monoclonal Antibodies Against Receptor Peptides

Synthetic peptides are first coupled to keyhole limpet hemocyanin or another carrier protein by the method of Liu, et al. [Biochem. 18: 690 (1979)]. Rabbits and mice are immunized with the coupled peptides according to a schedule and dose such as that described by Altman et al [Proc. Nat'l Acad. Sci. 81: 2176 (1984)]. The titer of antisera against the peptides is monitored by the ELISA method [Altman, et al., Proc. Nat'l. Acad. Sci. 81: 2176 (1984)]or cellular immunofluorescence. Mice exhibiting antibody titer after several immunizations are sacrificed. Spleenocytes from these immunized mice are fused with drug marked myeloma cell lines by the method of Kohler and Milstein [Nature 256: 495 (1975)]. Hybridoma culture secreting antibodies specifically reactive with the immunizing peptide are selected and cloned by limiting dilution. These selected monoclonal antibodies are further tested for their reactivity with T cell receptor protein on live cells by indirect immunofluorescent assay and immunoprecipitation [Acuto et al., Cell 34: 717 (1983)].

Clinical Studies Using Anti-Receptor Antibodies

The anti-receptor monoclonals are used in typing disease-specific T cells at the disease site or in peripheral lymphoid organs by reacting the monoclonals with T cells in a lung tumor specimen obtained from patients, or with T cells from biopsy samples or blood of patients and those of normal controls. A variety of methods such as immunoperoxidase staining and immunofluorescence staining may be employed. [Janossey et al., Nature 288: 81 (1980); Bhan, et al., J. Immunol., 129: 1578 (1982)]. The monoclonal antibodies so made react specifically against a portion of T cells invading lung carcinomas at definable stages of the disease. Furthermore, the monoclonal antibodies interfere with the killing of lung tumor cells by killer T cell clones or with the proliferative response of helper T4+T cell clones.

ADDITIONAL EXPERIMENTS

The procedure described in the Fourth Series of Experiments may be utilized to obtain monoclonal antibodies against the $\beta$ chain of T cell receptors associated with other diseases or with transplantation antigens. To do so, the T cell receptor (antigen-specific) genes are isolated from T cell clones known to be implicated in such situations. The following is a list of references describing T cell clones which may be so used:
1. Hepatitis B virus
   E. Celis, P. K. Kung and T. W. Chang (1984) J. Immunology 132: 1511
   "Hepatitis B virus—reactive Human T Lymphocyte Clones: Antigen Specificity and Helper Function for Antibody Synthesis".
2. Transplantation Antigens
   A. S. C. Meuer, S. F. Schlossman, and E. L. Reinherz (1982) Proc. Nat'l. Acad. Sci. USA 79: 4590
   "Clonal Analysis of Human Cytotoxic T Lymphocytes: T4 + and T8 + effector T Cells Recognize Products of Different Major Histocompatibility Complex Regions"
   B. T. G. Mayer, A. A. Fuller, T. C. Fuller, A. I. Lazarovits, L. A. Boyle and J. T. Kurnick (1985) J. Immunol 134: 258
   "Characterization of in vivo activated Allospecific T Lymphocytes propagated from Human Renal Allograft Biopsies Undergoing Rejection"
3. Herpes Simplex Virus
   D. D. Eckels, P. Lake, J. R. Lamib et al., (1983) Nature 301: 716
   "SB-Restricted Presentation of Influenza and Herpes Simplex Virus Antigens to Human T Lymphocyte Clones"
4. Generic Tumor Antigens
   G. P. Pawelee, M. R. Hadam, A. Ziegler, J. Lohmeyef, A. Rehbein, J. Kynsbier and P. Wernet (1982). J. Immunol. 128: 1892
   "Long Term Culture, Cloning and Surface Markers of Mixed Leukocyte Culture-derived Human T Lymphocytes with Natural Killer-like Cytotoxicity"
5. Rheumatoid Arthritis
   D. Duke, G. S. Panayi, G. Janossy and L. W. Poulter (1982) Clin. Exp. Immunol. 49: 22
   "An Immunohistological Analysis of Lymphocyte Subpopulations and their Microenvironment in the Synovial Membranes of Patients with Rheumatoid Arthritis Using Monoclonal Antibodies".

6. Allergens (Raqweed Antiqen E)

S. C. Meuer, D. A. Cooper, J. C. Hoagon, R. E. Hussey, K. A. Fitzgerald, S. F. Schlossman and E. L. Reinherz (1983) Science 222: 1239

"Identification of the Antigen of MHC-receptor on Human Inducer T Lmphocytes"

7. Acetylcholine Receptor in Myasthenia Gravis

F. Sinigaglin, C. Gotti, P. Ricirardi and F. Clementi, (1984) Proc. Nat'l. Acad. Sci 81: 7569

"Acetylcholine Receptor Specific Suppressive T Cell Factor from a Retrovirally Transformed T Cell Line"

8. Human Parasite Antigen

T. B. Nutman, D. J. Volkman, R. Hussain, A. S. Fanci, and E. A. Ottesen (1985) J. Immunol. 134: 1178.

9. Myelin in Basic Protein

J. Burns, A. Rosenzweig, B. Zweiman and R. P. Lisak (1983) Cellular Immunol. 82: 435.

What is claimed is:

1. A method of diagnosing a specific disease in a subject which comprises:
  a. obtaining from the subject suspected of having the specific disease a suitable sample containing T cells;
  b. contacting the sample under appropriate conditions with a reagent (1) capable of binding to T cells and (2) indicative of the presence of, and having specificity for, a unique amino acid sequence within the variable region of the β chain of the T cell receptor, the presence of an increased number of cells carrying the unique sequence relative to the number of cells carrying the sequence present in a normal subject being associated with the specific disease, so as to form a detectable complex between the reagent and T cells which contain the unique sequence and are present in the sample; and
  c. quantitatively determining the number of the T cells carrying the sequence present in the complex, comparing the number so determined with the number of T cells carrying the sequence determined for a normal subject using the same procedure and thereby diagnosing the specific disease.

2. A method of claim 1, wherein the specific disease is a cancer.

3. A method of claim 2, wherein the cancer is a human breast cancer.

4. A method of claim 2, wherein the cancer is a human colon cancer.

5. A method of claim 2, wherein the cancer is a human lung cancer.

6. A method of claim 2, wherein the cancer is a human lymphoma.

7. A method of claim 2, wherein the cancer is a human hepatoma.

8. A method of claim 2, wherein the cancer is a human leukemia.

9. A method of claim 1, wherein the specific disease is an autoimmune disease.

10. A method of claim 9, wherein the autoimmune disease is rheumatoid arthritis.

11. A method of claim 9, wherein the autoimmune disease is type 1 diabetes.

12. A method of claim 9, wherein the autoimmune disease is multiple sclerosis.

13. A method of claim 9, wherein the autoimmune disease is systemic lupus erythematosis.

14. A method of claim 9, wherein the autoimmune disease is myasthenia gravis or Graves disease.

15. A method of claim 1, wherein the specific disease is a degenerative disease of the nervous system.

16. A method of claim 1, wherein the specific disease is an infectious disease.

17. A method of claim 16, wherein the infectious disease is caused by a virus.

18. A method of claim 17, wherein the virus is HTLV-I or HTLV-III (LAV).

19. A method of claim 17, wherein the virus is HSV-I or HSV-II.

20. A method of claim 17, wherein the virus is hepatitis A or hepatitis B.

21. A method of claim 17, wherein the virus is cytomegalovirus.

22. A method of claim 16, wherein the infectious disease is caused by a yeast.

23. A method of claim 22, wherein the yeast is of the genus Candida.

24. A method of claim 16, wherein the infectious disease is caused by a parasite.

25. A method of claim 24, wherein the parasite is a schistosome.

26. A method of claim 24, wherein the parasite is filaria or mycobacterium.

27. A method of claim 24, wherein the parasite is Trichinella spiralis.

28. A method of claim 24, wherein the parasite is a protozoan which causes malaria.

29. A method of claim 24, wherein the parasite is a trypanosome which causes sleeping sickness.

30. A method of claim 15, wherein the infectious disease is caused by a bacterium.

31. A method of claim 30, wherein the bacterium produces tetanus toxoid.

32. A method of claim 1, wherein the specific disease is an allergy.

33. A method of claim 32, wherein the allergy is a delayed type hypersensitivity or a contact hypersensitivity.

34. A method of claim 1, wherein the subject is a human.

35. A method of claim 1, wherein the subject is an animal.

36. A method of claim 1, wherein the sample is derived from whole blood.

37. A method of claim 1, wherein the sample is derived from tissue.

38. A method of claim 1, wherein the unique sequence is at least 10 amino acids in length and is present within the first 30 amino acids located at the N-terminus of a variable region of the β chain of the T cell receptor.

39. A method of claim 38, wherein the unique sequence is

Gly-Val-Ile-Gln-Ser-Pro-Arg-His-Glu-Val-Thr-Glu-Met-Gly-Gln-Glu-Val-Thr-Leu-Arg-Cys.

40. A method of claim 1, wherein the reagent is an antibody directed to an epitope corresponding to the unique amino acid sequence.

41. A method of claim 4, wherein the antibody is a monoclonal antibody.

42. A method of claim 1, wherein the reagent is a DNA hybridization probe of at least about 30 bases and is complementary to the DNA sequence which encodes the unique amino acid sequence.

43. A method of claim 1, wherein the reagent is a RNA hybridization probe of at least about 30 bases and is complementary to the DNA sequence which encodes the unique amino acid sequence.

44. A method of claim 40, wherein the monoclonal antibody is labeled with a detectable moiety.

45. A method of claim 44, wherein the detectable moiety is a fluorescent dye.

46. A method of claim 44, wherein the detectable moiety is a radioactive isotope.

47. A method of claim 44, wherein the detectable moiety is an enzyme which catalyzes a reaction producing a detectable product.

48. A method of claim 44, wherein the detectable moiety is biotin.

49. A method of claim 44, wherein the detectable moiety is a metal ion detectable by nuclear magnetic resonance.

50. A method of claim 42, wherein the DNA hybridization probe is labeled with a detectable moiety.

51. A method of claim 43, wherein the RNA hybridization probe is labeled with a detectable moiety.

52. A method of claim 45, wherein the quantitive determination of the number of T cells carrying the sequence present in the complex is by fluorescence activated cell sorting.

53. A method of claim 15, wherein the degenerative disease is Alzheimer's disease.

54. A monoclonal antibody capable of binding to T cells and having specificity for a unique amino acid sequence contained within the variable region of the β chain of the T cell receptor, the presence of increased number of T cells carrying the unique sequence relative to the number of T cells carrying the sequence present in a normal subject being associated with a specific disease.

55. A monoclonal antibody capable of binding to T cells and having specificity for a unique amino acid sequence within the variable region of the β chain of the T cell receptor, the presence of increased numbers of T cells carrying the unique sequence relative to the number of T cells carrying the sequence present in a normal subject being associated with rejection of a transplanted organ.

56. A purified polypeptide having the sequence:

Gly-Val-Ile-Gln-Ser-Pro-Arg-His-Glu-Val-Thr-Glu-Met-Gly-Glu-Glu-Val-Thr-Leu-Arg-Cys.

57. A method for detecting organ transplant rejection in a subject into whom an organ from a different subject is transplanted which comprises:
  a. obtaining from the subject into whom the organ from a different subject has been transplanted a suitable sample containing T cells;
  b. contacting the sample under appropriate conditions with a reagent (1) capable of binding to T cells and (2) indicative of the presence of, and having specificity for, a unique amino acid sequence within the variable region of the β chain of the T cell receptor, the presence of an increased number of cells carrying the unique sequence relative to the number of cells carrying the sequence present in a normal subject being associated with organ transplant rejection, so as to form a detectable complex between the reagent and T cells which contain the unique sequence and are present in the sample; and
  c. quantitatively determining the number of the T cells carrying the sequence present in the complex, comparing the number so determined with the number of T cells carrying the sequence determined for a normal subject using the same procedure and thereby detecting organ transplant rejection.

* * * * *